United States Patent
Pichiorri et al.

(10) Patent No.: US 10,022,342 B2
(45) Date of Patent: Jul. 17, 2018

(54) METHODS AND COMPOSITIONS FOR TREATING MULTIPLE MYELOMA

(71) Applicant: Ohio State Innovation Foundation, Columbus, OH (US)

(72) Inventors: Flavia Pichiorri, Columbus, OH (US); Craig Hofmeister, Upper Arlington, OH (US)

(73) Assignee: OHIO STATE INNOVATION FOUNDATION, Columbus, OH (US)

( * ) Notice: Subject to any disclaimer, the term of this patent is extended or adjusted under 35 U.S.C. 154(b) by 0 days.

(21) Appl. No.: 15/254,900

(22) Filed: Sep. 1, 2016

(65) Prior Publication Data
US 2017/0056346 A1 Mar. 2, 2017

Related U.S. Application Data

(60) Provisional application No. 62/213,493, filed on Sep. 2, 2015.

(51) Int. Cl.
*A61K 31/454* (2006.01)
*A61K 31/167* (2006.01)

(52) U.S. Cl.
CPC .......... *A61K 31/167* (2013.01); *A61K 31/454* (2013.01)

(58) Field of Classification Search
None
See application file for complete search history.

(56) References Cited

U.S. PATENT DOCUMENTS 8,318,808 B2 11/2012 Chen

OTHER PUBLICATIONS

Roccaro, et al., MicroRNAs 15a and 16 regulate tumor proliferation in multiple myeloma. Blood. 2009; 113:6669-6680.
Kraj, et a., Flow cytometric immunophenotypic characteristics of 36 cases of plasma cell leukemia. Leuk Res. 2011; 35:169-176.
Kim, et al., Cell surface expression and functional significance of adhesion molecules on human myeloma-derived cell lines. Br J Haematol. 1994; 87:483-493.
Ghosh, et al., CD44: a validated target for improved delivery of cancer therapeutics. Expert Opin Ther Targets. 2012; 16:635-650.
Skubitz, Adhesion molecules. Cancer Treat Res. 2002; 107:305-329.
Hao, et al., Co-expression of CD147 (EMMPRIN), CD44v3-10, MDR1 and monocarboxylate transporters is associated with prostate cancer drug resistance and progression. Br J Cancer. 2010; 103:1008-1018.
Chen, et al. Coexpression of invasive markers (uPA, CD44) and multiple drug-resistance proteins (MDR1, MRP2) is correlated with epithelial ovarian cancer progression. Br J Cancer. 2009; 101:432-440.
Miletti-Gonzalez, et al.,The CD44 receptor interacts with P-glycoprotein to promote cell migration and invasion in cancer. Cancer Res. 2005; 65:6660-6667.
Zhao, et al. miR-30-5p functions as a tumor suppressor and novel therapeutic tool by targeting the oncogenic Wnt/—catenin/BCL9 pathway. Cancer Res. 2014; 74:1801-1813.
Al-Hajj, et al., Prospective identification of tumorigenic breast cancer cells. Proc Natl Acad Sci U S A. 2003; 100:3983-3988.
Bourguignon, et al. Hyaluronan-CD44 interaction promotes oncogenic signaling, microRNA functions, chemoresistance, and radiation resistance in cancer stem cells leading to tumor progression. Adv Cancer Res. 2014; 123:255-275.
Bourguignon,et al., Stem cell marker (Nanog) and Stat-3 signaling promote MicroRNA-21 expression and chemoresistance in hyaluronan/CD44-activated head and neck squamous cell carcinoma cells. Oncogene. 2012; 31:149-160.
Hofmeister, et al., Phase I Study of AR-42 in Relapsed Multiple Myeloma and Lymphoma. ASH Annual Meeting Abstracts, Abstract #2955. 2012.
Hideshima, et al., Rational combination treatment with histone deacetylase inhibitors and immunomodulatory drugs in multiple myeloma. Blood cancer journal. 2015; 5:e312.
Zhao, et al., A feedback regulatory loop involving microRNA-9 and nuclear receptor TLX in neural stem cell fate determination. Nature Structural & Molecular Biology. 2009; 16:365-371.
Senyuk., et al., Critical role of miR-9 in myelopoiesis and EVI1-induced leukemogenesis. Proceedings of the National Academy of Sciences of the United States of America. 2013; 110:5594-5599.
Thiele, et al., miR-9 enhances IL-2 production in activated human CD4(+) T cells by repressing Blimp-1. European journal of immunology. 2012; 42:2100-2108.
Nie, et al., MicroRNA-mediated down-regulation of PRDM1/Blimp-1 in Hodgkin/Reed-Stemberg cells: a potential pathogenetic lesion in Hodgkin lymphomas. Am J Pathol. 2008; 173:242-252.
Stessman, et al., Bortezomib resistance can be reversed by induced expression of plasma cell maturation markers in a mouse in vitro model of multiple myeloma. PLoS One. 2013; 8:e77608.
Zoller, et al., CD44, Hyaluronan, the Hematopoietic Stem Cell, and Leukemia-Initiating Cells. Front Immunol. 2015; 6:235.
Huber, et al., Variance stabilization applied to microarray data calibration and to the quantification of differential expression. Bioinformatics. 2002; 1:S96-104.
Yeung, et al., Clustering gene-expression data with repeated measurements. Genome biology. 2003; 4:R34.
Godar, et al., Growth-inhibitory and tumor-suppressive functions of p53 depend on its repression of CD44 expression. Cell. 2008; 134:62-73.
Chou, Drug combination studies and their synergy quantification using the Chou-Talalay method. Cancer Res 70:440-6, 2010.
Canella, et al., HDAC inhibitor AR-42 decreases CD44 expression and sensitizes myeloma cells to lenalidomide. Oncotarget 6:31134-50, 2015.
Roccaro, et al., MicroRNAs 15a and 16 regulate tumor proliferation in multiple myeloma. Blood 113:6669-80, 2009.

(Continued)

*Primary Examiner* — Heidi Reese
(74) *Attorney, Agent, or Firm* — Potomac Law Group, PLLC; Jeremy A. Cubert, Esq.

(57) ABSTRACT

Methods and compositions for sensitizing multiple myeloma cells to treatment with IMiDs are provided. Aspects include methods of administering AR-42 and an IMiD (e.g., lenalidomide, pomalidomide) to multiple myeloma patients.

12 Claims, 15 Drawing Sheets

(56) References Cited

OTHER PUBLICATIONS

Kronke et al., Lenalidomide induces ubiquitination and degradation of CK1alpha in del(5q) MDS. Nature 523:183-8, 2015.

Lu, et al., Efficacy of a novel histone deacetylase inhibitor in murine models of hepatocellular carcinoma, Hepatology. Oct. 2007;46(4):1119-30.

Kumar, et al., Immunophenotyping in multiple myeloma and related plasma cell disorders. Best Practice & Research Clinical Haematology. 2010; 23:433-451.

Fonseca et al., J. Prognostic factors and staging in multiple myeloma. Hematology/oncology clinics of North America. 2007; 21:1115-1140.

Fonseca et al., International Myeloma Working Group molecular classification of multiple myeloma: spotlight review. Leukemia. 2009; 23:2210-2221.

Kapoor et al., Impact of risk stratification on outcome among patients with multiple myeloma receiving initial therapy with lenalidomide and dexamethasone. Blood. 2009; 114:518-521.

Nair et al., Superior results of Total Therapy 3 (2003-33) in gene expression profiling-defined low-risk multiple myeloma confirmed in subsequent trial 2006-66 with VRD maintenance. Blood. 2010; 115:4168-4173.

Cavo et al., Bortezomib with thalidomide plus dexamethasone compared with thalidomide plus dexamethasone as induction therapy before, and consolidation therapy after, double autologous stem-cell transplantation in newly diagnosed multiple myeloma: a randomised phase 3 study. Lancet. 2010; 376:2075-2085.

Kumar et al., Improved survival in multiple myeloma and the impact of novel therapies. Blood. 2008; 111:2516-2520.

Palumbo, Towards a new standard of care for patients with myeloma? The lancet oncology. 2010; 11:3-4.

Palumbo, et al., Melphalan, prednisone, and lenalidomide for newly diagnosed myeloma: kinetics of neutropenia and thrombocytopenia and time-to-event results. Clinical lymphoma & myeloma. 2009; 9:145-150.

Gay, et al. Lenalidomide plus dexamethasone versus thalidomide plus dexamethasone in newly diagnosed multiple myeloma: a comparative analysis of 411 patients. Blood. 2010; 115:1343-1350.

Lionetti et al., Integrative high-resolution microarray analysis of human myeloma cell lines reveals deregulated miRNA expression associated with allelic imbalances and gene expression profiles. Genes Chromosomes Cancer. 2009; 48:521-531.

Lionetti et al., Identification of microRNA expression patterns and definition of a microRNA/mRNA regulatory network in distinct molecular groups of multiple myeloma. Blood. 2009; 114:e20-26.

Pichiorri, et al., MicroRNAs regulate critical genes associated with multiple myeloma pathogenesis. Proceedings of the National Academy of Sciences of the United States of America. 2008; 105:12885-12890.

Maes, et al., Epigenetic modulating agents as a new therapeutic approach in multiple myeloma. Cancers. 2013; 5:430-461.

Dimopoulos, et al., The role of epigenetics in the biology of multiple myeloma. Blood cancer journal. 2014; 4:e207.

Mitsiades, et al. Transcriptional signature of histone deacetylase inhibition in multiple myeloma: biological and clinical implications. Proceedings of the National Academy of Sciences of the United States of America. 2004; 101:540-545.

Richardson, et al., Phase I trial of oral vorinostat (suberoylanilide hydroxamic acid, SAHA) in patients with advanced multiple myeloma. Leukemia & lymphoma. 2008; 49:502-507.

Damiano, et al., Cell adhesion mediated drug resistance (CAM-DR): role of integrins and resistance to apoptosis in human myeloma cell lines. Blood. 1999; 93:1658-1667.

Bourguignon, et al., Hyaluronan-CD44 interaction with protein kinase C (epsilon) promotes oncogenic signaling by the stem cell marker Nanog and the Production of microRNA-21, leading to down-regulation of the tumor suppressor protein PDCD4, anti-apoptosis, and chemotherapy resistance in breast tumor cells. J Biol Chem. 2009; 284:26533-26546.

Chikamatsu, et al., Alteration of cancer stem cell-like phenotype by histone deacetylase inhibitors in squamous cell carcinoma of the head and neck. Cancer science. 2013; 104:1468-1475.

Dimopoulos, et al., Vorinostat or placebo in combination with bortezomib in patients with multiple myeloma (Vantage 088): a multicentre, randomised, double-blind study. The Lancet Oncology. 2013; 14:1129-1140.

San-Miguel, et al., Phase Ib study of panobinostat and bortezomib in relapsed or relapsed and refractory multiple myeloma. Journal of clinical oncology: official journal of the American Society of Clinical Oncology. 2013; 31:3696-3703.

Biran, et al., A Phase II, Single-Center, Open-Label Study of Oral Panobinostat in Combination With Lenalidomide and Weekly Dexamethasone in Patients With Multiple Myeloma. Blood. 2013; 122:5392.

Richter, et al., Salvage Therapy with Vorinostat, Lenalidomide, and Dexamethasone (ZRD) in Lenalidomide/Dexamethasone Relapsed/Refractory Multiple Myeloma. ASH Annual Meeting Abstracts. 2011; 118:3986.

Kulp, et al., Antitumor effects of a novel phenylbutyrate-based histone deacetylase inhibitor, (S)-HDAC-42, in prostate cancer. Clinical cancer research: an official journal of the American Association for Cancer Research. 2006; 12:5199-5206.

Zhang, et al., The novel histone deacetylase inhibitor, AR-42, inhibits gp130/Stat3 pathway and induces apoptosis and cell cycle arrest in multiple myeloma cells. International Journal of Cancer Journal International du Cancer. 2011; 129:204-213.

Bjorklung, et al., Evidence of a role for CD44 and cell adhesion in mediating resistance to lenalidomide in multiple myeloma: therapeutic implications. Leukemia. 2014; 28:373-383.

Naor, et al., CD44: structure, function, and association with the malignant process. Adv Cancer Res. 1997; 71:241-319.

Josefsson, et al., Prostate cancer increases hyaluronan in surrounding nonmalignant stroma, and this response is associated with tumor growth and an unfavorable outcome. Am J Pathol. 2011; 179:1961-1968.

Gritsenko, et al., Interstitial guidance of cancer invasion. J Pathol. 2012; 226:185-199.

Lee, et al., Acetylation and activation of STAT3 mediated by nuclear translocation of CD44. The Journal of Cell Biology. 2009; 185:949-957.

Kim, et al., CD19-CD45 low/—CD38 high/CD138+ plasma cells enrich for human tumorigenic myeloma cells. Leukemia. 2012; 26:2530-2537.

Lin, et al., AR-42, a novel HDAC inhibitor, exhibits biologic activity against malignant mast cell lines via down-regulation of constitutively activated Kit. Blood. 2010; 115:4217-4225.

Lucas, et al., The novel deacetylase inhibitor AR-42 demonstrates pre-clinical activity in B-cell malignanciesin vitro and in vivo. PLoS One. 2010; 5:e10941.

Woan, et al., Modulation of antigen-presenting cells by HDAC inhibitors: implications in autoimmunity and cancer. Immunology and Cell Biology. 2012; 90:55-65.

Ohwada, et al., CD44 and hyaluronan engagement promotes dexamethasone resistance in human myeloma cells. European journal of haematology. 2008; 80:245-250.

Lee, et al., The nuclear RNase III Drosha initiates microRNA processing. Nature. 2003; 425:415-419.

Fortina, et al. Digital mRNA profiling. Nat Biotechnol. 2008;26:293-294.

Lewis, et al., Prediction of mammalian microRNA targets. Cell. 2003; 115:787-798.

Krek, et al., Combinatorial microRNA target predictions. Nat Genet. 2005; 37:495-500.

Vikesaa, et al.RNA-binding IMPs promote cell adhesion and invadopodia formation. The EMBO Journal. 2006; 25:1456-1468.

Schaeffer, et al., Insulin-like growth factor 2 mRNA binding protein 3 (IGF2BP3) overexpression in pancreatic ductal adenocarcinoma correlates with poor survival. BMC cancer 2010; 10:59.

Miranda, et al., A pattern-based method for the identification of MicroRNA binding sites and their corresponding heteroduplexes. Cell. 2006; 126:1203-1217.

(56) References Cited

OTHER PUBLICATIONS

Chou, Drug combination studies and their synergy quantification using the Chou-Talalay method. Cancer Res. 2010; 70:440-446.

Manier, et al., Bone marrow microenvironment in multiple myeloma progression. Journal of biomedicine & biotechnology. 2012; 2012:157496.

Romano, et al., Immunological dysregulation in multiple myeloma microenvironment. Biomed Res Int. 2014; 2014:198539.

Dalton, The tumor microenvironment: focus on myeloma. Cancer Treat Rev. 2003; 1:11-19.

Chen et al., Clinical Pharmacokinetics and Pharmacodynamics of Lenalidomide, Clin. Pharmacokinet, Jun. 28, 2016.

Tseng, et al., Preclinical Investigation of the Novel Histone Deacetylase Inhibitor AR-42 in the Treatment of Cancer-Induced Cachexia. J Natl Cancer Inst 107, 2015.

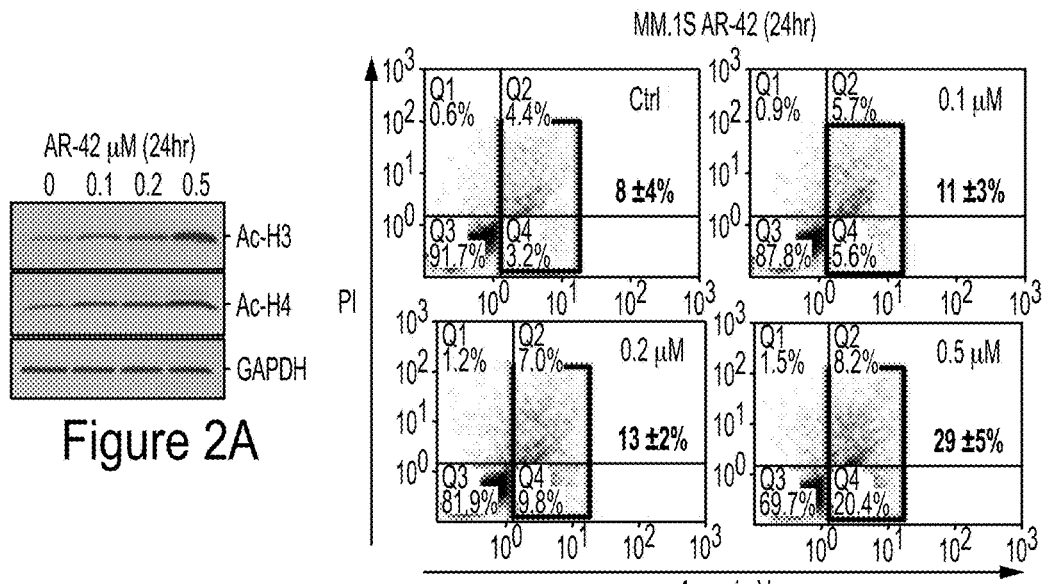
Figure 2A
Figure 2B
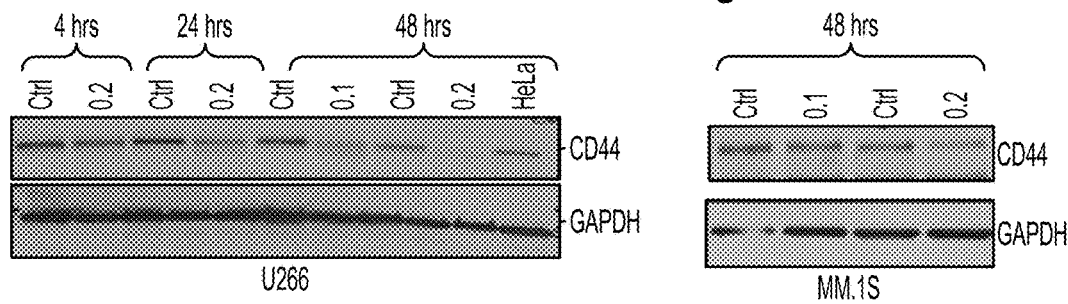
Figure 2C
Figure 2D
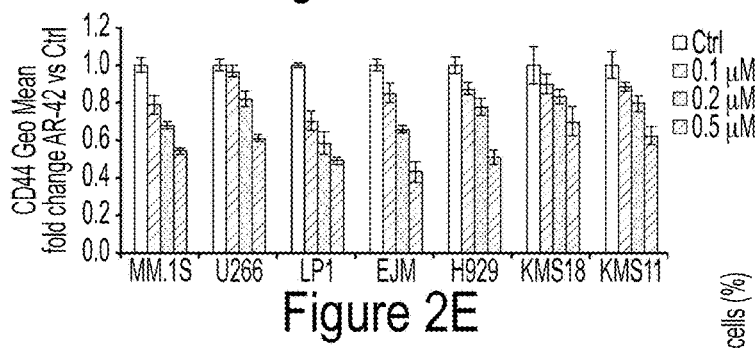
Figure 2E
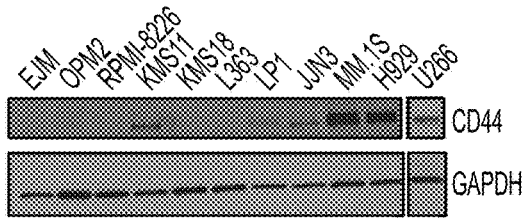
Figure 2F
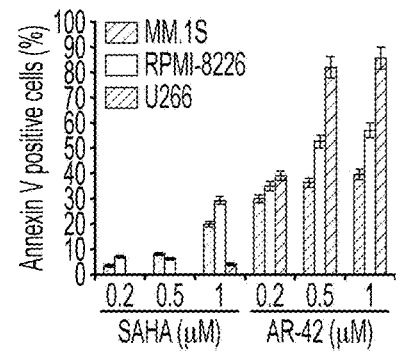
Figure 2G

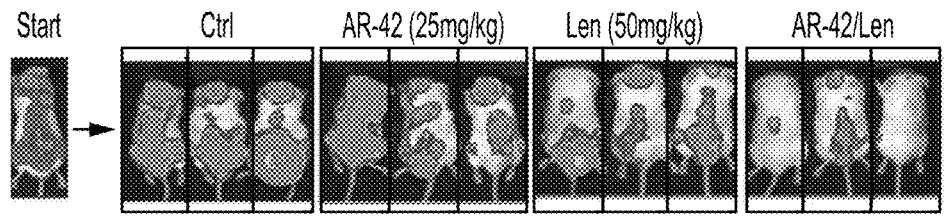
Figure 10A
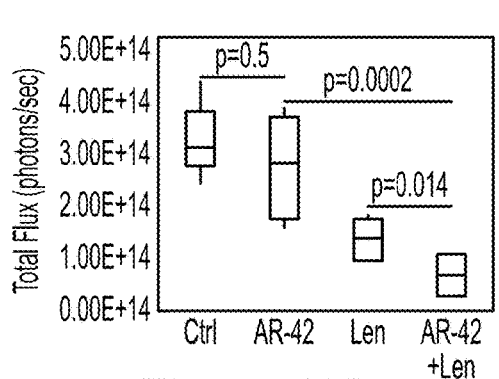
Figure 10B
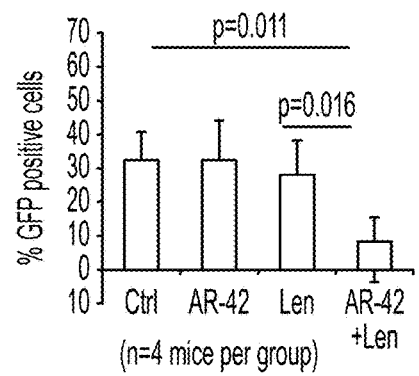
Figure 10C
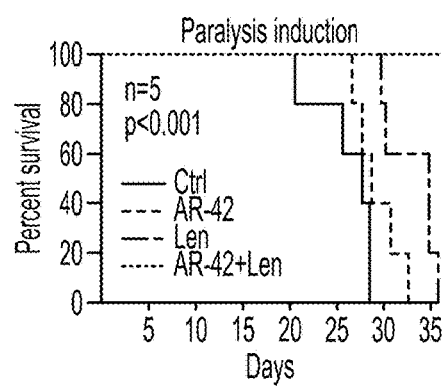
Figure 10D
| Treatment comparisons | p-value |
|---|---|
| AR-42 vs Ctrl | p=0.4 |
| Len vs Ctrl | p=0.08 |
| AR-42+Len vs Ctrl | p<0.0001 |
| AR-42+Len vs AR-42 | p=0.0025 |
| AR-42+Len vs Len | p=0.03 |
Figure 10E Supplementary Table S1: Differentially expressed genes upon AR-42 treatment of MM.1S cells

| Gene ID | log2_Fold Change AR-42 vs. Ctrl |
|---|---|
| IRF7 | -4.15 |
| CD3EAP | -3.60 |
| ICOSLG | -2.09 |
| TFRC | -1.12 |
| MX1 | -1.04 |
| CSF2RB | -1.02 |
| PTPN6 | -0.93 |
| ADA | -0.75 |
| TUBB | -0.73 |
| TP53 | -0.63 |
| SLAMF7 | -0.60 |
| CD44 | -0.50 |
| CD28 | -0.38 |
| HLA-B | -0.10 |
| HLA-DRA | 0.14 |
| APP | 0.17 |
| CD164 | 0.33 |
| CD99 | 0.41 |
| IRF1 | 0.51 |
| STAT3 | 0.53 |
| TNFAIP3 | 0.60 |
| LITAF | 0.64 |
| ITGB1 | 0.79 |
| MAPKAPK2 | 0.85 |
| IRAK4 | 0.89 |
| CCL3 | 1.19 |
| NFKBIZ | 1.43 |
| STAT4 | 1.95 |
| PTPN22 | 2.20 |
| CD40 | 2.32 |
| CXCL10 | 2.49 |
| CD81 | 5.44 |
| ABCB1 | 5.57 |

Unsupervised hierarchical clustering analysis of nCounter® GX Human Immunology assays on MM.1S cells treated with AR-42 0.1 µM treatment for 24 hrs. Data are showed as expression of the majority of the immunology-related genes with $p$-value < 0.001

Figure 11

Supplementary Table S2: Differentially expressed miRNAs upon AR-42 treatment of MM.1S cells

| microRNA_ID | 0.1 μM vs. Ctrl | Adjusted p-values (0.1 μM vs. Ctrl) | 0.2 μM vs. Ctrl | Adjusted p-values (0.2 μM vs. Ctrl) |
|---|---|---|---|---|
| hsa-miR-1973 | 11.45 | 1.13E-04 | 4.87 | 1.41E-04 |
| hsa-miR-342-3p | 9.74 | 1.75E-03 | 9.08 | 1.20E-04 |
| hsa-miR-4516 | 8.09 | 1.94E-03 | 9.30 | 6.48E-05 |
| hsa-miR-4284 | 7.29 | 2.20E-02 | 2.96 | 4.25E-02 |
| hsa-miR-664-3p | 6.06 | 6.53E-03 | 8.00 | 1.48E-04 |
| hsa-miR-4485 | 5.92 | 2.18E-02 | 4.49 | 4.99E-03 |
| hsa-miR-30a-5p | 5.46 | 1.49E-02 | 4.65 | 1.91E-03 |
| hsa-miR-575 | 5.28 | 1.51E-02 | 5.28 | 1.09E-03 |
| hsa-miR-22-3p | 5.22 | 9.03E-04 | 4.98 | 5.73E-05 |
| hsa-miR-494 | 4.44 | 1.51E-02 | 5.22 | 5.08E-04 |
| hsa-miR-630 | 4.19 | 1.64E-04 | 2.58 | 1.93E-04 |
| hsa-miR-30d-5p | 3.65 | 1.43E-03 | 2.83 | 3.98E-04 |
| hsa-miR-146a-5p | 2.70 | 1.13E-04 | 2.83 | 3.18E-06 |
| hsa-miR-26b-5p | 2.67 | 1.28E-05 | 2.73 | 2.42E-07 |
| hsa-miR-320a | 2.58 | 2.14E-02 | 2.14 | 6.35E-03 |
| hsa-miR-361-3p | 2.43 | 4.27E-03 | 2.67 | 1.31E-04 |
| hsa-miR-30e-5p | 2.27 | 1.30E-03 | 2.12 | 1.32E-04 |
| hsa-miR-186-5p | 1.95 | 1.30E-02 | 2.58 | 6.35E-05 |
| hsa-miR-9-5p | 1.82 | 4.93E-02 | 2.00 | 1.84E-03 |
| hsa-miR-30b-5p | 1.68 | 3.43E-03 | 1.43 | 2.84E-03 |
| hsa-miR-548aa | 0.46 | 1.09E-02 | 1.52 | 2.75E-02 |
| hsa-miR-1244 | 0.45 | 3.45E-02 | 1.25 | 3.08E-01 |
| hsa-miR-93-5p | 0.44 | 1.12E-04 | 0.39 | 1.16E-06 |
| hsa-miR-19b-3p | 0.44 | 7.53E-05 | 0.49 | 6.25E-06 |
| hsa-miR-20a-5p+20b-5p | 0.41 | 1.13E-04 | 0.45 | 1.16E-05 |
| hsa-miR-200c-3p | 0.40 | 3.26E-03 | 0.91 | 5.73E-01 |
| hsa-miR-365a-3p | 0.39 | 3.26E-03 | 0.94 | 7.27E-01 |
| hsa-miR-301a-3p | 0.36 | 2.72E-04 | 0.49 | 2.04E-04 |
| hsa-miR-18a-5p | 0.36 | 7.75E-05 | 0.47 | 2.91E-05 |
| hsa-miR-644a | 0.35 | 2.58E-02 | 1.59 | 1.01E-01 |
| hsa-miR-548ah-5p | 0.33 | 3.06E-02 | 2.32 | 1.21E-02 |
| hsa-miR-106a-5p+17-5p | 0.33 | 5.10E-07 | 0.36 | 3.46E-08 |
| hsa-miR-423-3p | 0.33 | 1.51E-02 | 1.20 | 4.64E-01 |
| hsa-miR-92a-3p | 0.28 | 2.03E-04 | 0.33 | 2.77E-05 |
| hsa-miR-4455 | 0.27 | 3.07E-02 | 1.18 | 6.35E-01 |

(Continued)

| microRNA_ID | 0.1 μM vs. Ctrl | Adjusted p-values (0.1 μM vs. Ctrl) | 0.2 μM vs. Ctrl | Adjusted p-values (0.2 μM vs. Ctrl) |
|---|---|---|---|---|
| hsa-miR-223-3p | 0.24 | 2.66E-02 | 1.22 | 5.83E-01 |
| hsa-miR-335-5p | 0.24 | 2.12E-02 | 1.57 | 2.05E-01 |
| hsa-miR-4454 | 0.23 | 2.82E-02 | 0.78 | 5.24E-01 |
| hsa-miR-720 | 0.21 | 3.45E-02 | 0.74 | 4.66E-01 |
| hsa-miR-193b-3p | 0.20 | 3.40E-04 | 1.43 | 1.07E-01 |
| hsa-miR-450a-5p | 0.18 | 3.26E-03 | 0.93 | 8.17E-01 |
| hsa-miR-411-5p | 0.17 | 5.84E-04 | 1.46 | 1.35E-01 |
| hsa-miR-221-3p | 0.13 | 2.76E-04 | 0.53 | 3.16E-02 |
| hsa-miR-3676-3p | 0.07 | 1.69E-05 | 0.60 | 3.89E-02 |
| hsa-miR-126-3p | 0.07 | 2.10E-07 | 0.30 | 3.77E-06 |

Unsupervised hierarchical clustering analysis of global miRNA expression in MM.1S cells treated by 0.1 μM, or 0.2 μM AR-42 for 24 hours and compared to DMSO treated cells (Ctrl)

Figure 12

Supplementary Table S3: Combinatorial index (CI) of AR-42 + Len

| AR-42 (µM) | Len (µM) | CI |
|---|---|---|
| 0.1 | 2.5 | 0.52 |
| 0.1 | 5.0 | 0.45 |
| 0.1 | 10.0 | 0.42 |
| 0.2 | 2.5 | 0.48 |
| 0.2 | 5.0 | 0.43 |
| 0.2 | 10.0 | 0.35 |

Proliferation MTT assay was performed on MM.1S cells treated with AR-42 (50 nM, or 100 nM) in combination with lenalidomide (Len; 1 µM, 2.5 µM, and 10 µM). Combinatorial indices (CI) were calculated by the Chou-Talalay method. All data are expressed as mean of three independent sets of experiments

Figure 13

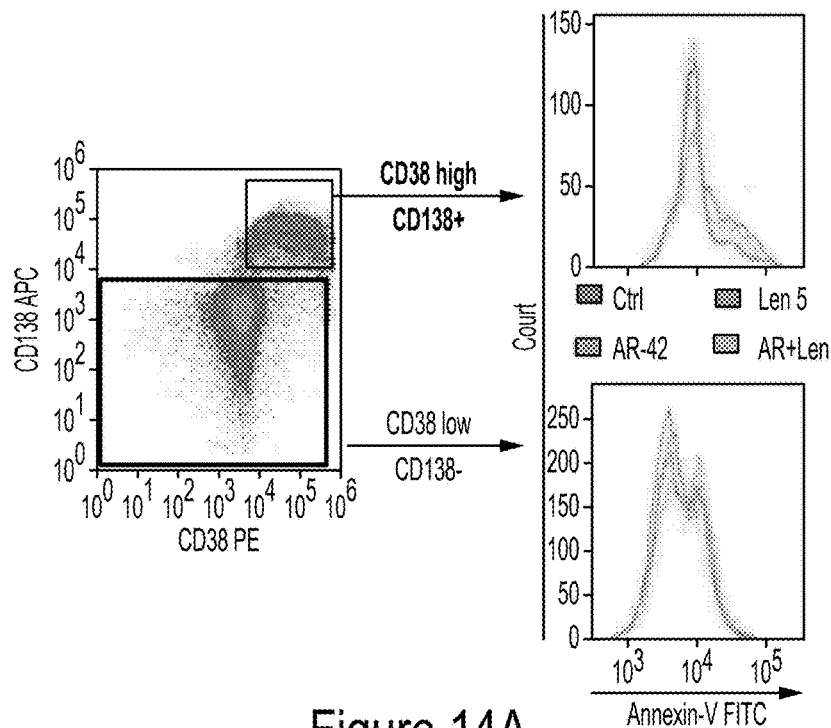

Figure 14A

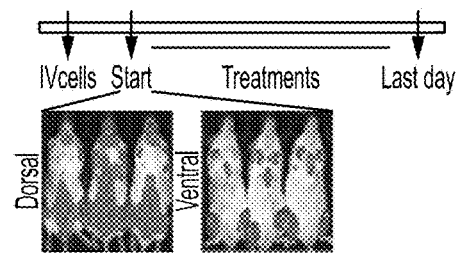

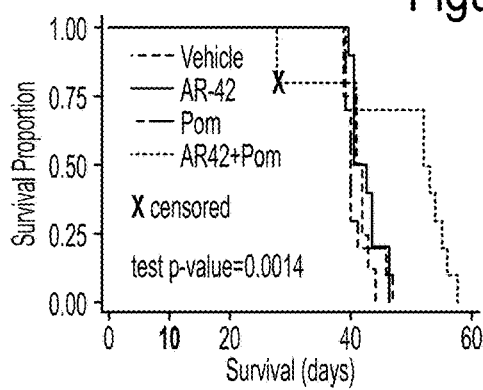

Figure 14D

Fig.11 A) Strategy of apoptosis analysis by flow cytometry of MM BM samples treated with with 0.2 μM AR-42, 5μM Len, or with AR-42+Len. Flow cytometric Annexin-V assay of CD38high/CD138+ MM cells of 5 Len refractory MM patients and 3 newly diagnosed MM patients. Statistical differences between the treatments for all 8 patients are reported (B), as we published (3); C) Scheme of treatment showing the level of MM cell engraftment at the day 10 when the treatments started; D) The survival experience of mice treated with AR42+Pom is significantly improved (logrank test p-value=0.0014).

SEQUENCE LISTING

```
<160> NUMBER OF SEQ ID NOS: 7

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gctagccacc tacaccatta tcttg                                           25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gctagcaatt cttggtgttg ttatg                                           25

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tctttggtta tctagctgta tga                                             23

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cagaggcaga tgccaaacgg ggtacagatt gcttaacc                             38

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggttaagcaa tctgtacccc gtttggcatc tgcctctg                             38
```

```
<210> SEQ ID NO 6
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
gcagaugcca aaccaaaga                                                  19

<210> SEQ ID NO 7
<211> LENGTH: 19
<212> TYPE: RNA
<213> ORGANISM: Homo sapiens

<400> SEQUENCE: 7
ucuuugguua ucuagcugu                                                  19
```

METHODS AND COMPOSITIONS FOR TREATING MULTIPLE MYELOMA

PRIORITY CLAIM

This application claims priority to U.S. Provisional Patent Application Ser. No. 62/213,493 filed on Sep. 2, 2015. The above referenced provisional patent application is incorporated herein by reference as if restated in full. All references cited herein, including, but not limited to patents and patent applications, are incorporated by reference in their entirety.

GOVERNMENT RIGHTS

This invention was made with government support under Project 46050 590000 60029462 awarded by the National Cancer Institute, National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Sep. 30, 2016, is named 2242-00-009U01_SL.txt and is 1,800 bytes in size.

BACKGROUND

Multiple myeloma (MM) is a plasma cell (PC) neoplasm that accounts for more than 20,000 new cases every year in the United States [1-3]. Development of novel therapeutic options, such as proteasome inhibitors (PI) and immunomodulatory agents (IMiDs), has improved treatment outcomes. Patients eligible for bone marrow transplantation show 5 year survival in more than 70% of the cases, which is reduced to ~50% in the transplant ineligible patients [4, 5]. However, the overall survival of patients carrying high-risk MM cytogenetic abnormalities is still very poor and the patients inevitably relapse [3]. Alternative novel treatment strategies are, urgently needed [6-9]. Epigenetic modifications such as DNA methylation and histone acetylation, as well as microRNA deregulation, play important roles in the pathogenesis and treatment responses of MM [10-13].

Histone acetyltransferases and histone deacetylases (HDACs) affect a broad-array of genes involved in cell cycle, apoptosis, and protein folding [14]. The first FDA-approved deacetylase inhibitor (HDACi), suberoylanilide hydroxamic acid (SAHA, vorinostat), was shown to be effective in vitro and to have clinical efficacy in T-cell lymphomas [15]. However, in MM, SAHA showed only minimal activity as a single agent [16]. For most HDACi's, the mechanism of action with respect to MM is unknown. However, at biologically achievable concentrations, it has been theorized that HDACi's can sensitize MM cells to other drugs by interfering with cell adhesion mediated drug resistance (CAM-DR) [17-19]. In two phase 1 trials, some patients with MM were effectively treated by a combination of HDACi's (SAHA, or panobinostat) with the proteasome inhibitor, bortezomib [20, 21]. However, phase 1/2 studies of combination of SAHA, or panobinostat with the immunomodulatory agent lenalidomide showed unacceptable tolerability and limited activity in lenalidomide-refractory patients [22, 23].

Recently, an orally bioavailable class I/II, phenylbutyrate-based HDAC inhibitor, AR-42 (ARNO Therapeutics, Flemington, N.J.) has been developed. AR-42 has greater anti-proliferative effects as compared to SAHA, in vitro and in vivo [24]. AR-42 also inhibits activation of STAT3, even in the presence of interleukin (IL)-6 activation signal, inducing apoptosis of MM cells [25].

Acetylation of core histones plays an important role in the regulation of gene transcription by controlling nucleosomal packaging of DNA. Deacetylation of histones results in tight packing of nucleosomes and transcriptional repression due to limited access of transcription factors to DNA targets. Histone acetylation relaxes nucleosome structures, providing greater access for transcription factors. The balance between histone deacetylation and acetylation is modulated by the histone deacetyl-transferases (HDACs) and histone acetyl-transferases (HAT). An abnormal balance of these factors is correlated with abnormal cell growth and several forms of cancer as discussed in U.S. Pat. No. 8,318,808, incorporated by reference herein in its entirety. HDAC inhibitors, in particular, change the balance between acetylation and deacetylation resulting in growth arrest, differentiation, and apoptosis in many tumor cell types. See, e.g., U.S. Pat. No. 8,318,808.

18 HDACs have been identified in humans and are characterized as being zinc dependent or nicotinamide adenine dinucleotide (NAD) dependent (Discov Med 10(54):462-470, November 2010) and are associated with the following classes: class I (HDACs 1, 2, 3, and 8); class II (HDACs 4, 5, 6, 7, 9, and 10; class III (sirtuins 1-7 (SIRT)); and class IV (HDAC 11). Id.

AR-42 is a broad-spectrum deacetylase inhibitor of both histone and non-histone proteins with demonstrated greater potency and activity in solid tumors and hematological malignancies when compared to vorinostat (i.e., SAHA). See, e.g., Lu Y S, et al., Efficacy of a novel histone deacetylase inhibitor in murine models of hepatocellular carcinoma, Hepatology. 2007 October; 46(4):1119-30; Kulp S K, et al., Antitumor effects of a novel phenylbutyrate-based histone deacetylase inhibitor, (S)-HDAC-42, in prostate cancer, Clin Cancer Res. 2006 Sep. 1; 12(17):5199-206.

Dexamethasone and lenalidomide resistance in MM has been attributed to upregulation of CD44 [26], a cell surface glycoprotein involved in cell adhesion, migration and cell-cell interactions [27]. CD44 functions as a receptor for hyaluronic acid (HA), which itself is considered a tumor marker in cancer [28, 29]. Moreover, CD44 forms a complex with STAT3 and p300 (acetyltransferase), causing STAT3 activation in a cytokine- and growth factor-independent manner [30]. Thus, pharmacological targeting of CD44 may affect different pathways in MM malignancies and be beneficial for patients with MM who are resistant to dexamethasone- and lenalidomide treatment.

SUMMARY

Multiple myeloma (MM) is a hematological malignancy of plasma cells in the bone marrow. Despite multiple treatment options, MM is inevitably associated with drug resistance and poor outcomes. Histone deacetylase inhibitors (HDACi's) are promising novel agents undergoing evaluation in clinical trials for the potential treatment of patients with MM. Although HDACi's have anti-myeloma activity, in the clinic, single-agent HDACi treatments have been of limited use due to low tolerability and low levels of activity.

As described herein, HDACi AR-42 downregulates CD44, a glycoprotein that has been associated with lenalidomide and dexamethasone resistance in myeloma both in vitro and in vivo. CD44 downregulation is shown to be mediated, in part, by miR-9-5p, targeting insulin-like growth factor 2 mRNA binding protein 3 (IGF2BP3), which directly binds to CD44 mRNA and increases its stability. Aspects described herein demonstrate that AR-42 enhances anti-myeloma activity of lenalidomide in primary MM cells isolated from MM patients resistant to lenalidomide treatment in an in vivo MM mouse model. Further aspects provide methods of overcoming lenalidomide resistance in patients with multiple myeloma by administering AR-42.

Aspects described herein demonstrate that AR-42 down-regulates CD44 protein and mRNA levels in vitro and in vivo. Without being bound by theory, it is believed that AR-42 decreases CD44 expression through the up-regulation of miR-9-5p, which directly targets and down-regulates the RNA binding protein IGF2BP3, known to physically bind to CD44 mRNA and increase its stability [31].

In another aspect, AR-42 increases the sensitivity of MM cells to lenalidomide in a mouse model, and the combination of both drugs has a synergistic effect in treating multiple myeloma.

Aspects described herein provide methods of sensitizing multiple myeloma cells to treatment with lenalidomide by administering AR-42 and lenalidomide to a patient in need treatment in an amount sufficient to achieve a blood or tissue concentration of at least about 0.5 to about 1 µM of AR-42 and at least about 391 to about 568 ng/ml ng/ml of lenalidomide.

Further aspects provide methods of treating a mammal with multiple myeloma comprising administering AR-42 and an IMiD to the mammal.

In one aspect, the IMiD is selected from the group consisting of lenalidomide and pomalidomide.

Aspects described herein also provide compositions comprising AR-42 and an IMiD (e.g., lenalidomide, pomalidomide).

FIGURES

FIG. 2A shows an exemplary immunoblot analysis of acetyl histone H3 and H4 expression in MM.1S cells treated with 0.1 to 0.5 µM AR-42 for 24 hours;

Figure 3A:
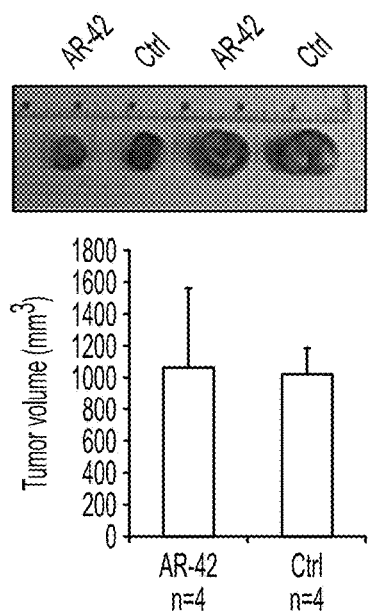
Figure 3B:
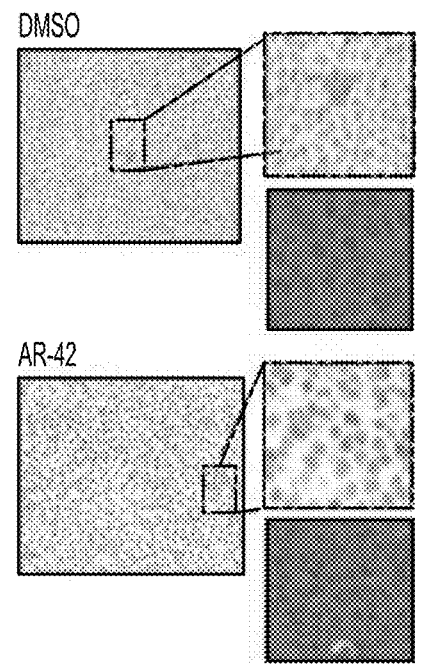
Figure 3C:
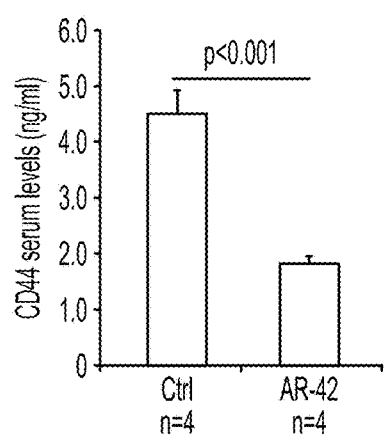
Figure 3D:
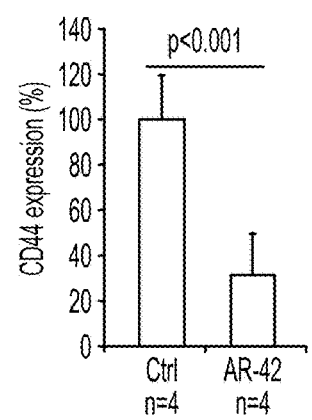
Figure 4:
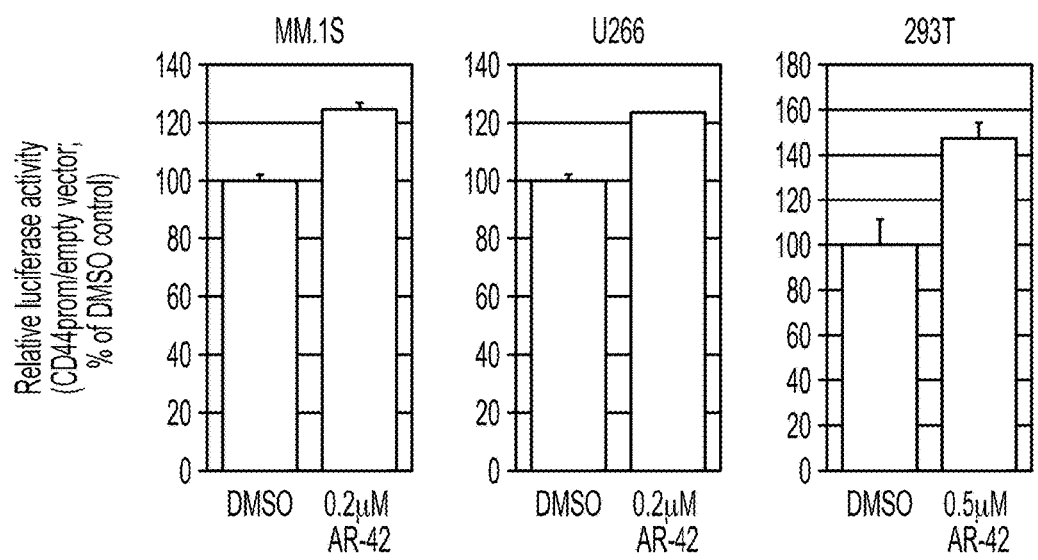
Figure 5A:
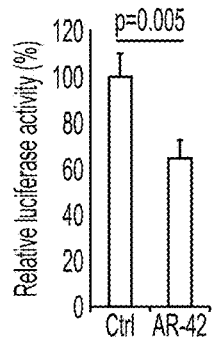
Figure 5B:
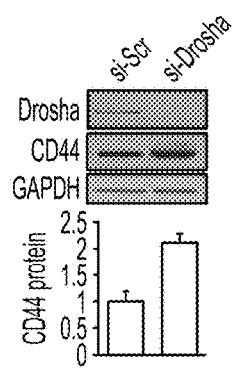
Figure 5C:
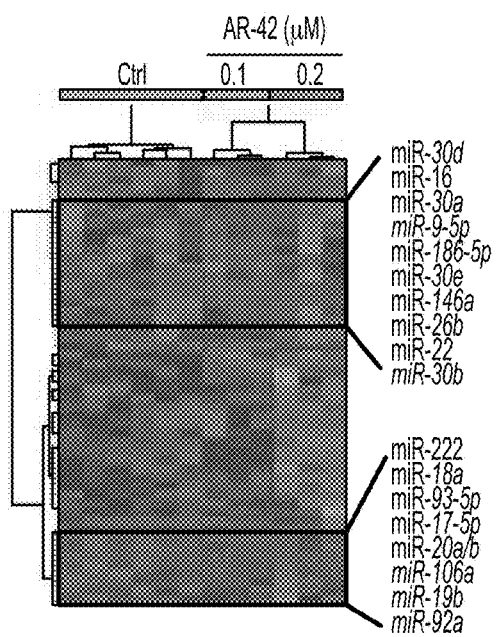
Figure 5D:
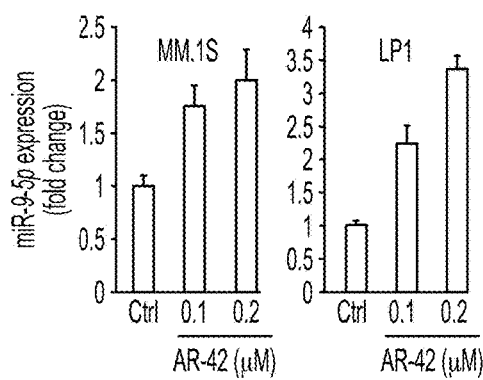
Figure 5E:
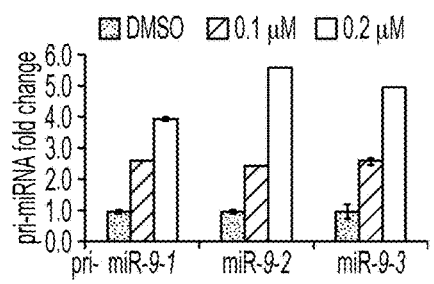
Figure 6:
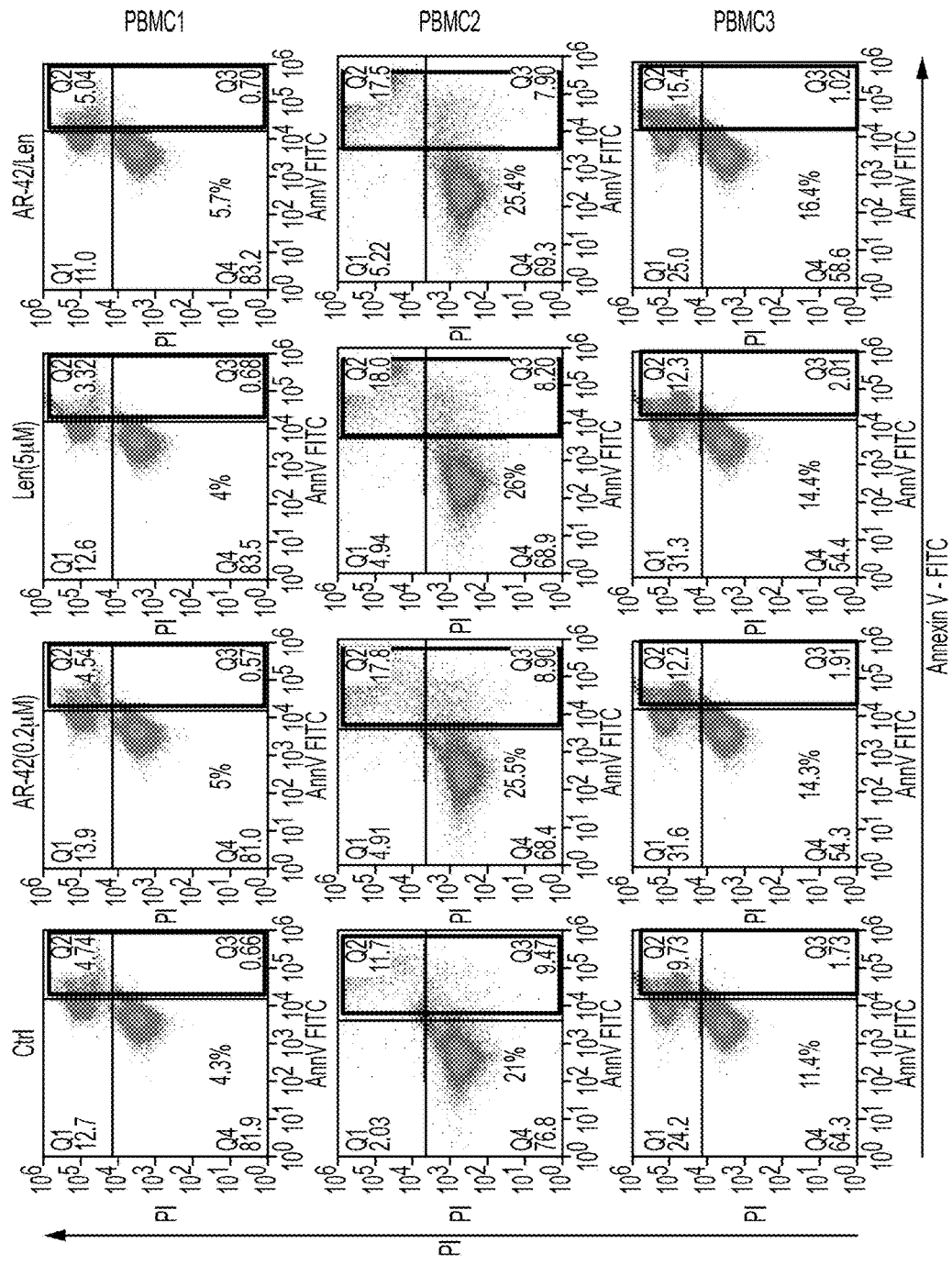
Figure 7A:
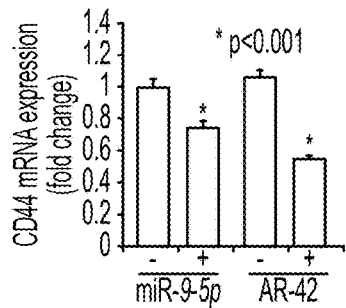
Figure 7B:
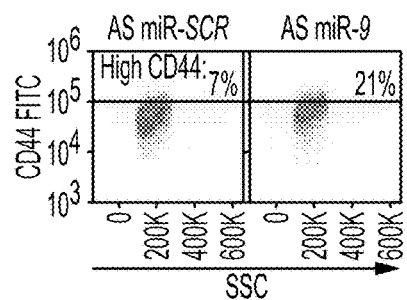
Figure 7C:
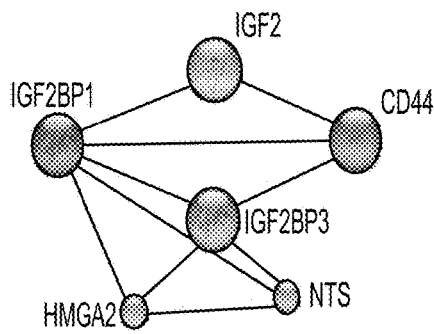
Figure 7D:
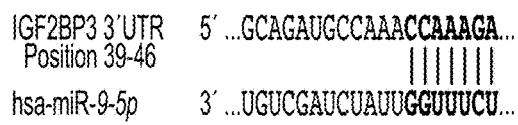
Figure 7E:
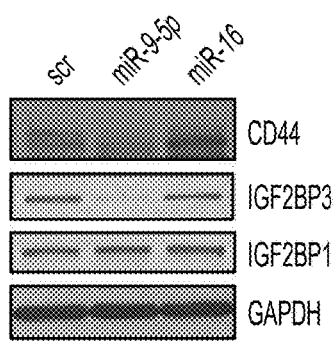
Figure 7F:
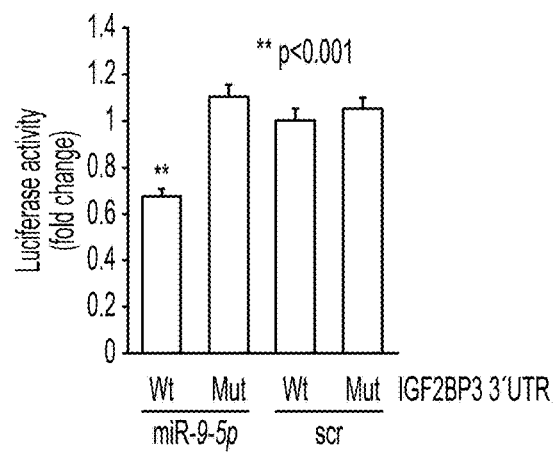
Figure 8:
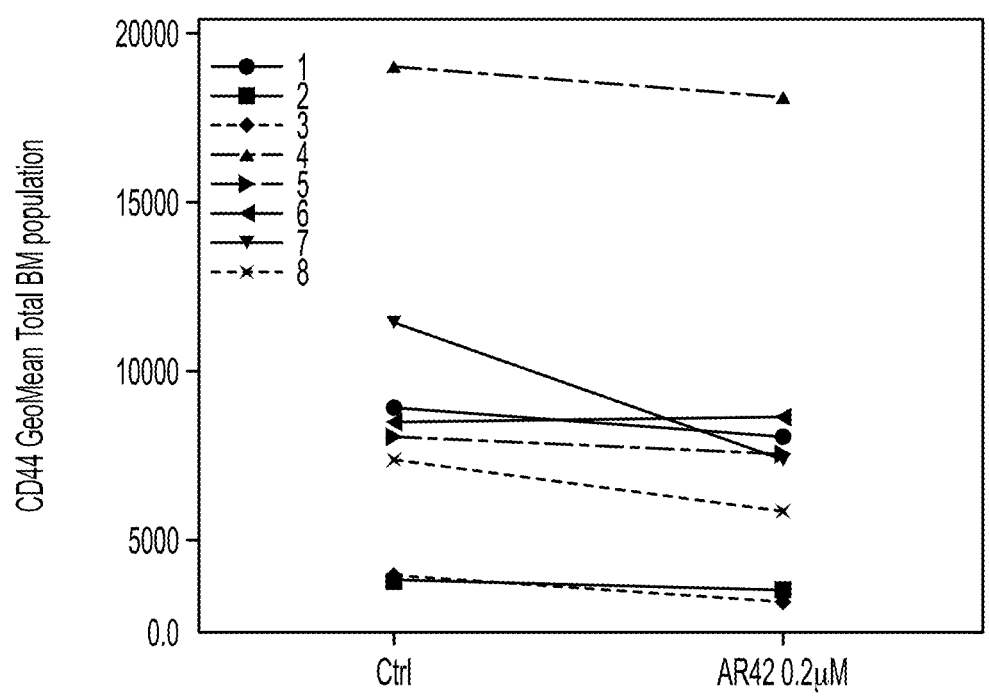
Figure 9A:
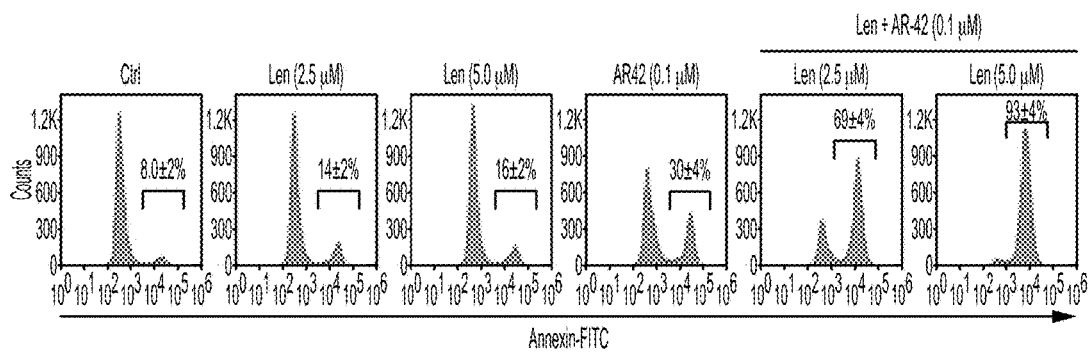
Figure 9B:
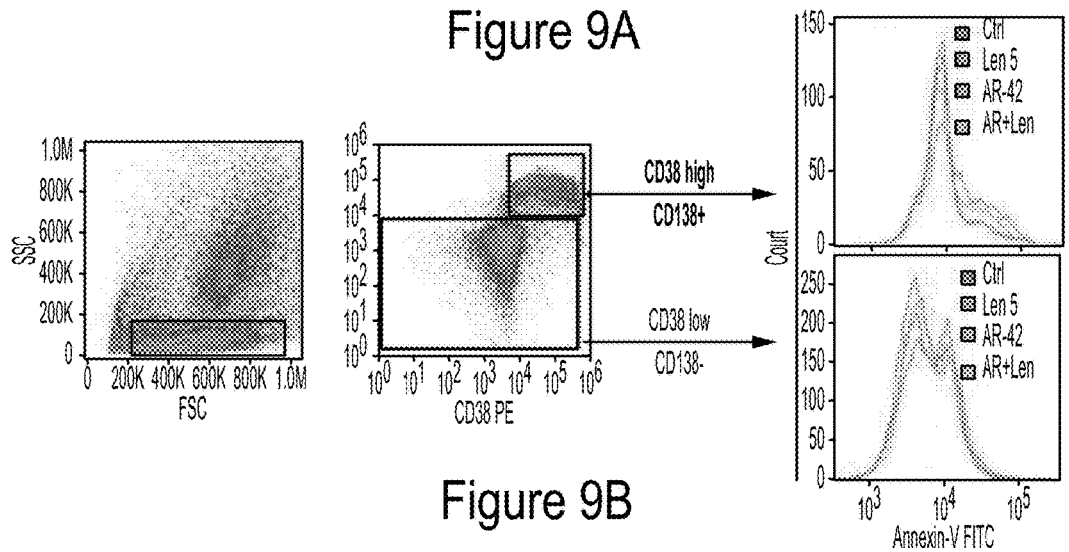
Figure 9C:
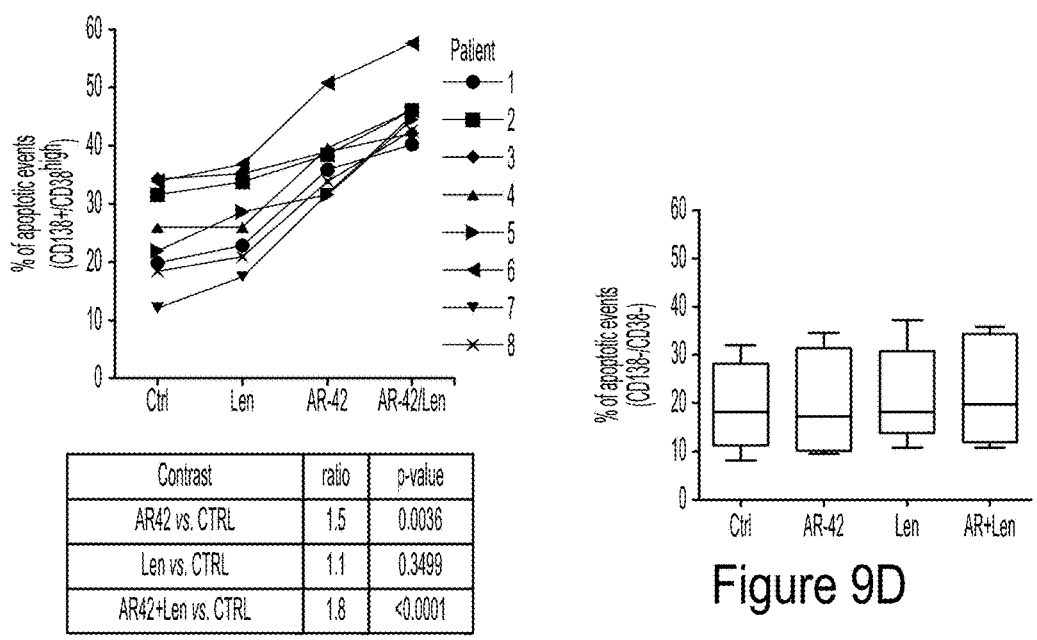
Figure 9D:
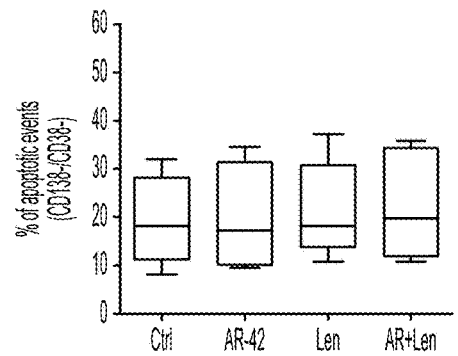
Figure 15:
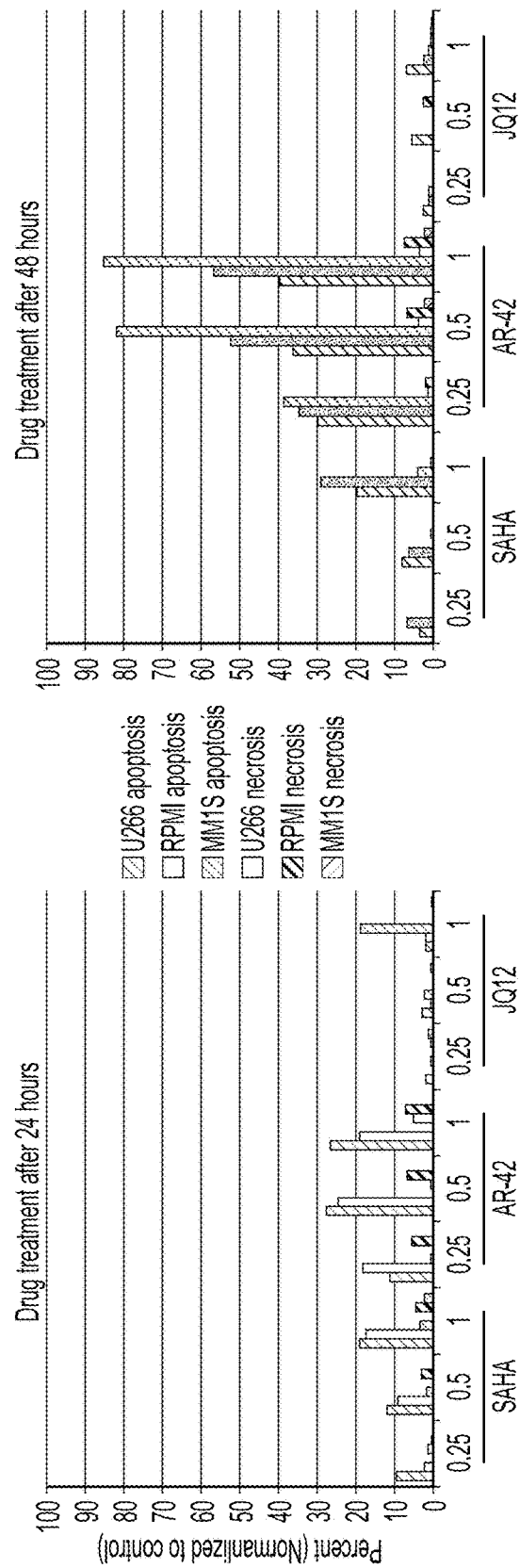

FIG. 2B shows induction of apoptosis in MM.1S cells treated with 0.1, 0.2, and 0.5 µM AR-42 for 24 hours measured by Annexin V-P1 staining and flow cytometric analyses;

FIG. 2C shows an exemplary western blot of CD44 expression in U266 cells treated with AR-42 (0.1, 0.2, and 0.5 µM);

FIG. 2D shows an exemplary western blot of CD44 expression in MM.1S cells treated with AR-42 (0.1, 0.2, and 0.5 µM);

FIG. 2E shows the exemplary results of flow cytometry analyses of CD44 expression in LP1, MM.1S, H929, EJM, KMS11, and U266 cells;

FIG. 2F shows an exemplary western blot analysis of CD44 protein expression in EJM, OPM-2, RPMI-8226, KMS11, KMS18, L363, LP1, JJN3, MM.1S, H929, and U266 cell lines;

FIG. 2G shows an exemplary comparison of apoptosis induced by treatment of U266, RPMI-8226, and MM.1S cells treated for 248 hours with SAHA (0.25, 0.5, and 1.0 µM) or AR-42 (0.1, 0.2, and 0.5 µM);

FIG. 3A shows exemplary tumor volume measurements for tumors excised from mice injected with MM.1S cells treated with 2 doses of AR-42 (25 mg/kg) or vehicle control;

FIG. 3B shows CD44 expression of the tumors (IHC staining) as described above with respect to FIG. 3A;

FIG. 3C provides soluble serum levels of CD44 from the tumors described above with respect to FIG. 3A as quantified by ELISA;

FIG. 3D provides the percentage of CD44 expression from the tumors described above with respect to FIG. 3A;

FIG. 4 shows that downregulation of CD44 by AR-42 is not mediated by the promoter region and shows exemplary luciferase activity of a CD44 reporter vector in MM.1S, U266, and 293T cells treated with AR-42 at the indicated concentration or DMSO vehicle control;

FIG. 5A shows the results of an exemplary luciferase activity in MM.1S cells transfected with pGL3-CD44 3'UTR construct and treated for 24 hours with 0.2 µM AR-42 or vehicle control;

FIG. 5B shows CD44 protein levels in MM.1S cells treated with RNA silencing for Drosha (si-Drosha) or unrelated sequence (si-Scr) as analyzed by Western blot using anti-Drosha and anti-CD44 antibodies;

FIG. 5C shows an exemplary dendrogram of the unsupervised hierarchical clustering analysis of global miRNA expression in MM.1S cells treated with the indicated concentrations of AR-42, or vehicle control;

FIG. 5D shows an exemplary assay of miR-9-5p expression in MM.1S (left) and LP1 (right) cells treated with AR-42 at 0.1 and 0.2 µM or vehicle control as determined by qRT-PCR (real-time polymerase chain reaction);

FIG. 5E shows the exemplary effects of 24 hour treatment of MM.1S cells with AR-42 at indicated concentrations on expression of pri-miR-9-1, pri-miR-9-2, and pri-miR-9-3 as determined by qRT-PCR;

FIG. 6 shows the effects of AR-42 and Lenalidomide (Len) alone or in combination on apoptosis in PBMC from multiple myeloma patients who were treated ex vivo with 0.2 µM AR-42 and 5 µM Len as single agents or in combination for 48 hours as measured by Annexin V-PI staining using a flow cytometer;

FIG. 7A shows the exemplary CD44 expression in MM.1S cells transfected with miR-9-5p or negative control miR precursor (Ctrl) as measured by qRT-PCR;

FIG. 7B shows an exemplary bivariate dot plot of CD44 expression in MM.1S cells transfected with AS miR-SCR or AS miR-9 as determined by flow cytometry;

FIG. 7C shows an exemplary diagram based on STRING database showing functional interaction networks between IGF2BP1, IGF2BP3, and CD44;

FIG. 7D illustrates the IGF2BP3 3'UTR containing the seed sequence for miR-9-5p (SEQ ID NOS 6-7, respectively, in order of appearance);

FIG. 7E shows an exemplary Western blot for levels of IGF2BP3 and IGF2BP1 in L363 cells transfected with miR-9-5p, miR-16, or scramble control;

FIG. 7F shows luciferase reporter expression levels in MM.1S cells transfected with reporter genes containing IGF2BP3 3'UTR, either wild type or mutant at the predicted miR-9-5p binding site and co-transfected with miR-9-5p precursor or negative controls;

FIG. 8 shows the efficacy of AR-42/Len on CD44 levels in total bone marrow specimens from 5 Len refractory and 3 newly diagnosed MM patients treated with 0.2 µM AR-42 for 48 hours as evaluated by flow cytometry;

FIG. 9A shows Annexin V expression by flow cytometry in MM.1S cells treated twice every 24 hours with Len (2.5 or 5.0 AR-42 (0.1 µM), or a combination of Len and AR-42 as indicated;

FIG. 9B shows an exemplary apoptosis analysis strategy by flow cytometry in bone marrow samples including staining bone marrow cells from 5 Len refractory and 3 newly diagnosed MM patients with anti-CD138 and anti-CD38 antibodies followed by sorting into two populations with each population being treated with control, 5 µM Len, 0.25 µM AR-42, a combination of both drugs for 48 hours followed by a flow cytometric Annexin V apoptosis assay;

FIG. 9C shows an exemplary Annexin V induction in $CD38^{high}$/CD138+MM cells treated as described with respect to FIG. 9B;

FIG. 9D shows flow cytometric evaluation of apoptosis in $CD38^{1'}$/CD138–bone marrow cells from the same MM patients described with respect to FIG. 9C;

FIG. 10A luminescence images for NOD-SCID mice engrafted with 5×108 MM.1S GFP+/Luc+ cells and treated for 3 weeks with vehicle control, AR-42, Len, or AR-42/Len combination;

FIG. 10B shows tumor progression as evaluated by bioluminescence imaging in the mice as described with respect to FIG. 10A;

FIG. 10C shows an exemplary analysis of murine bone marrow tumor progression by CD138-GFP+quantification by flow cytometry;

FIG. 10D shows Kaplan-Meier survival curves for mice as described with respect to FIG. 10A;

FIG. 10E compares p-values associated with the treatment groups as described with respect to FIG. 10A;

FIG. 11 shows differentially expressed genes resulting from treatment of MM.1S cells with AR-42;

FIG. 12 shows differentially expressed miRNAs resulting from treatment of MM.1S cells with AR-42;

FIG. 13 shows the combinatorial index of cells treated with AR-42 plus Len;

FIG. 14A shows an exemplary apoptosis analysis strategy of multiple myeloma (MM) bone marrow (BM) samples treated with 0.2 µM AR-42, 5 µM Len or with AR-42+Len by a flow cytometric Annexin V assay of CD38high/CD138+MM cells from 5 Len refractory MM patients and 3 newly diagnosed MM patients;

FIG. 14B shows the statistical differences between the eight patients described with respect to FIG. 14A;

FIG. 14C shows an exemplary scheme of treatment and the level of MM cell engraftment on day 10 when treatments started;

FIG. 14D shows the survival experience of mice treated with AR-42 plus pomalidomide (Pom); and FIG. 15 shows the effect of three HDAC inhibitors (SAHA, AR-42, and JQ12) on apoptosis and cell necrosis in vitro in the indicated cells lines after 24 and 48 hours of treatment at the indicated concentration (0.25, 0.5, and 1 µM).

DETAILED DESCRIPTION

Before describing several exemplary aspects described herein, it is to be understood that the invention is not limited to the details of construction or process steps set forth in the following description. The aspects described herein are capable of being practiced or being carried out in various ways.

Aspects described herein provide methods of sensitizing multiple myeloma cells to treatment with lenalidomide by administering AR-42 and lenalidomide to a patient in need treatment in an amount sufficient to achieve a blood or tissue concentration of at least about 0.5 to about 1 µM of AR-42 and at least about 391 to about 568 ng/ml ng/ml of lenalidomide.

In another aspect, the amount of AR-42 administered to the patient is about 40 to 70 mg per day in a single dose or divided dose, three times per week for three weeks out of a 28 day cycle. In yet another aspect, the amount of lenalidomide administered to the patient is about 25 mg per day for days 1-21 of a 28 day cycle. In another aspect, the amount of AR-42 administered to the patient is about 0.6 to about 1.1 mg/kg of the patient.

Further aspects provide methods of treating a mammal with multiple myeloma by administering AR-42 and an IMiD to the mammal.

In this aspect, the amount of AR-42 administered to the mammal is about 40 to 70 mg in a single dose or divided dose, three times per week for three weeks out of a 28 day cycle. In another aspect, the amount of AR-42 administered to the patient is about 0.6 to about 1.1 mg/kg of the patient.

In another aspect, AR-42 and the IMiD are co-administered to the mammal. In yet another aspect, AR-42 is administered before administering the IMiD. In a further aspect, the IMiD is administered before administering AR-42.

The IMiD can be selected from the group consisting of lenalidomide and pomalidomide (Pom). In this aspect, the amount of lenalidomide administered to the mammal can be about 25 mg per day for days 1-21 of a 28 day cycle. In another aspect, the amount of pomalidomide administered to the mammal is about 4 mg per day.

Further aspects provide pharmaceutical compositions comprising AR-42 and an IMiD. The IMiD can be selected from the group consisting of lenalidomide and pomalidomide.

HDAC inhibitors described in U.S. Pat. No. 8,318,808 can be used in various methods and compositions described herein. These HDAC inhibitors are based on, for example, fatty acids coupled with Zn2+-chelating motifs through aromatic Ω-amino acid linkers. In various aspects, the HDAC inhibitors may have the formula:

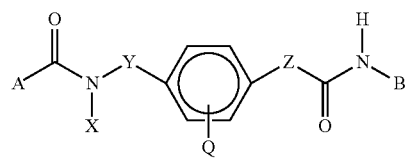

wherein X is chosen from H and CH3; Y is (CH2)n wherein n is 0-2; Z is chosen from (CH2)m wherein m is 0-3 and (CH)2; A is a hydrocarbyl group; B is o-aminophenyl or hydroxyl group; and Q is a halogen, hydrogen, or methyl.

In another aspect, methods described herein utilize AR-42, also known as (S)-N-hydroxy-4-(3-methyl-2-phenylbutanamido)benzamide having the following chemical structure:

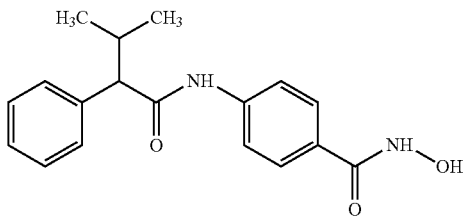 [SMILES: CC(C)C(C(=O)Nc1ccc(C(=O)NO)cc1)c1ccccc1]

In yet another aspect, AR-42 includes salts, solvates, hydrates, anhydrous, co-crystalline and other crystalline forms and combinations. AR-42 can be formulated into a variety of dosage forms having increased stability, increased bioavailability, sustained release, and other properties.

AR-42 Down-Modulates CD44 in Myeloma Cells

Growth inhibitory and pro-apoptotic properties of AR-42 as a single agent treatment agent have been reported previously [25, 32, 33] in numerous malignancies, including MM. Because of the potent immunomodulatory effects observed with classical pan-HDACi's [34], immunology-related gene networks altered upon AR-42 treatment in MM cells were investigated using nCounter technology to analyze the effects of AR-42 on the expression of 511 human genes in MM.1S cells following 24-hr treatment with 0.1 µM AR-42. This concentration was chosen because it provides a detectable hyperacetylation of histone 3 and 4 (FIG. 2A) without significant increase of apoptosis, as measured by Annexin V-PI staining in all MM cell lines tested (MM.1S, U266, RPMI-8226, MM.1R) (FIG. 2B and data not shown).

Figure 1A:
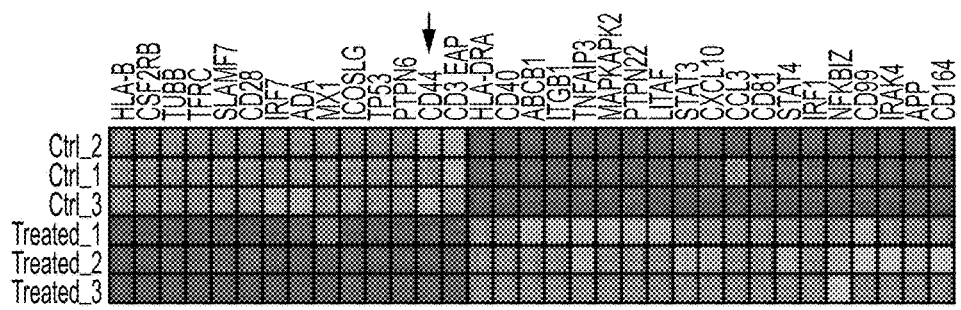
FIG. 1A shows an exemplary dendogram of the unsupervised hierarchical clustering analysis of nCounter GX Human Immunology assays in MM.1S cells treated with 0.1 µM AR-42 for 24 hours.

Unsupervised hierarchical clustering analysis identified two distinct branches corresponding to AR-42 treated and untreated cells (FIG. 1A), and showed that expression of numerous immunology-related genes was strongly altered (FIG. 1I). Among the most significantly downregulated genes (p<0.001) were several cell membrane associated proteins, including CD44 (FIG. 1I).

Figure 1B:
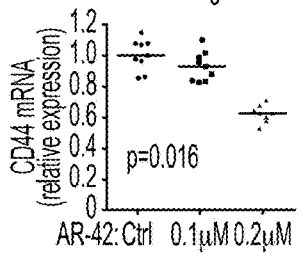
FIG. 1B shows CD44 mRNA expression measured by qRT-PCR in RNA from MM.1S cells treated for 24 hours with 0.1, or 0.2 µM AR-42.
Figure 1C:
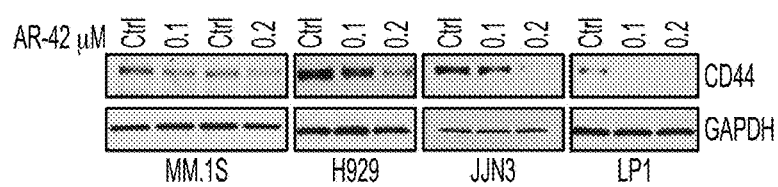
FIG. 1C shows CD44 protein expression in MM.1S, H929, JJN3, and LP1 cells treated with AR-42 at 0.1 and 0.2 µM.

CD44 expression in MM cells correlates with cell adhesion mediated drug resistance (CAM-DR) [17-19] and it has been shown to mediate resistance to dexamethasone [35] and lenalidomide [26]. qRT-PCR validation, showed that CD44 mRNA (FIG. 1B) and protein levels (FIG. 1C, FIG. 2C) were consistently downregulated by 24-hr treatment with AR-42 in a dose-dependent fashion compared to the vehicle control (DMSO; Ctrl). Reduction of CD44 mRNA and protein persisted for 48 hours after treatment (FIGS. 2C-2D and data not shown).

Figure 1D:
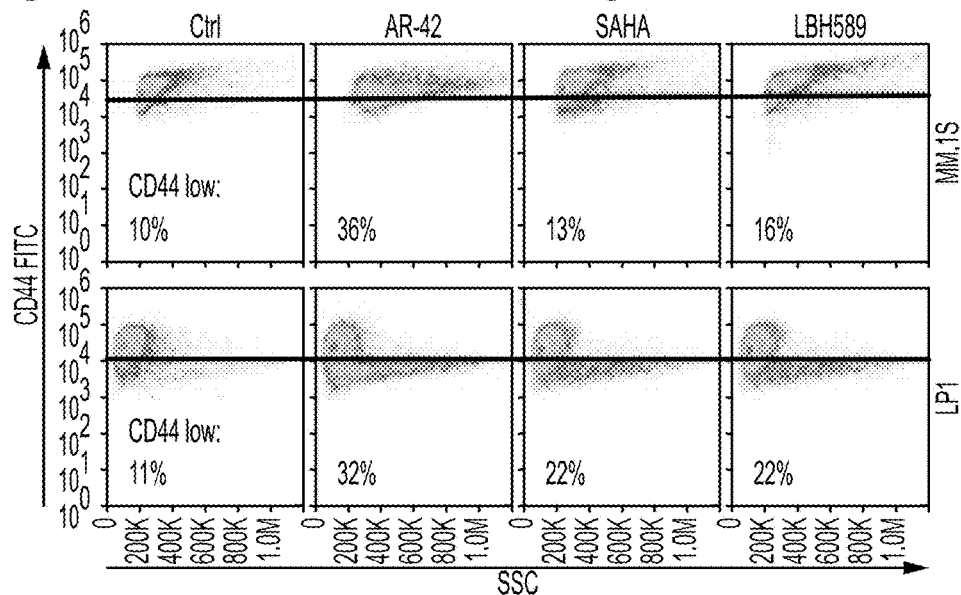
FIG. 1D shows an exemplary flow cytometry analysis of CD44 expression in MM.1S and LP1 cells after 24 hour treatment with AR-42 (0.2 SAHA (1 and LBH589 (LBH; 0.01 µM)

The down-regulation of CD44 cell surface expression was also observed by flow cytometry in all MM cell lines tested expressing detectable CD44 levels (FIG. 1D, FIGS. 2E-2F and data not shown). AR-42 treatment for 48 hours provided a consistent up-regulation of CD48 at protein and mRNA levels (FIG. 1E and data not shown), supporting the idea that AR-42 mediated CD44 down-regulation is not simply associated with a global down-regulation of the surface molecules of MM cells.

Figure 1E:
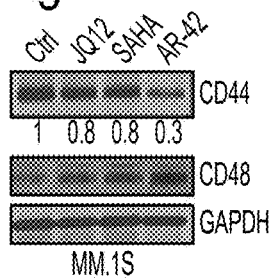
FIG. 1E shows exemplary results from the treatment of MM.1S cells with HDAC inhibitors (0.5 µM JQ12, 1 µM SAHA, or 0.2 µM AR-42) or vehicle control for 48 hours (Western Blot for CD44, Top Panel, stained with anti-CD48 antibody Middle Panel, and normalized for GAPDH, Bottom Panel)

AR-42 showed greater CD44 downregulation compared to HDACi's (e.g., SAHA, LBH589 and HDAC1/2 inhibitor (JQ12)) at comparable IC50 concentrations (0.2 µM AR-42, 1.0 µM SAHA, 0.01 µM LBH, and 0.5 µM JQ12) (FIG. 1D-1E, FIG. 2G).

AR-42 Decreases CD44 Levels In Vivo

To investigate if AR-42 treatment could affect CD44 expression in vivo, a xenograft MM mouse model was created by injecting 1×107 viable cells of MM.1S cell line subcutaneously into the right flank of 12 NOD-SCID mice. Three weeks later, a group of 8 mice containing comparable tumor size (250±60 mm3) was selected and randomly divided into 2 groups. One group of mice (n=4) received intra-peritoneal injections of 25 mg/kg AR-42, while the second group (n=4) was injected with vehicle control (8% DMSO in PBS; Ctrl). Injections were administered once a day (on Monday and Wednesday). Because the anti-tumor activity of AR-42 has been previously reported in preclinical mouse studies [33], mice were sacrificed 2 days after the second injection in order to avoid tumor size reduction. Indeed, at this time point the tumors were still comparable between the mouse groups (FIG. 3A). Tumors were excised and used for CD44 immunohistochemical (IHC) studies, while the serum was collected for ELISA assays. IHC analysis of tumor sections revealed that the AR-42-treated mice displayed significant lower CD44 staining compared with the control group (FIG. 3B). ELISA assays also showed decreased levels of soluble CD44 in the serum of the mice treated with AR-42 (FIG. 3C). Thus, AR-42 down-regulates CD44 directly in vivo.

AR-42 Modulates Expression of microRNAs in MM Cells

To address the molecular mechanism(s) responsible for downregulation of CD44 gene, the potential role of one or more cis regulatory regions was considered. Surprisingly, 24 hour treatment with 0.2 µM of AR-42 did not lower the activity of CD44 promoter region in MM cells (MM.1S, U266 and 293T) (FIG. 4). Therefore, the 3'UTR of CD44 was analyzed to determine if inhibition of CD44 expression by AR-42 was mediated by microRNA(s) upregulated by AR-42 treatment. The CD44 3'UTR element was subcloned downstream from the SV40 promoter-driven luciferase gene and transiently transfected the resulting reporter plasmid into MM.1S cells. Incubation of these cells with 0.2 µM AR-42 for 24 hours decreased luciferase activity detecting the activity of the CD44 3'UTR element by 35% as compared to untreated cells (FIG. 5A).

Since RNA ribonuclease, Drosha is important during the initial steps of microRNA processing [36], the effect of Drosha knock-down on CD44 expression using specific siRNA was investigated. As shown in FIG. 5B, inhibition of Drosha expression in MM.1S cells resulted in a 2-fold increase of CD44 protein levels. Thus, down-modulation of CD44 expression by AR-42 is believed to be mediated by CD44 3'UTR, and may involve upregulation of microRNA(s) targeting CD44 3'UTR.

To determine if miRNAs are regulated by AR-42 in MM cells at sub-lethal concentrations, a full-spectrum analysis of miRNA levels was performed using an array analysis of global miRNA expression on RNA from MM.1S cells grown in the presence or absence of AR-42 at different concentration (0.1, or 0.2 µM) for 24 hours. In this aspect, NanoString technology [37] with an expanded set of probes capable of assaying the expression of more than 800 human miRNAs was used to generate the date. FIG. 5C is a dendogram of an unsupervised hierarchical clustering analysis with samples segregated according to class of treatments.

51 miRNAs were differentially expressed between the two groups. 29 miRNAs were significantly down-regulated in cells treated with AR-42 and 22 were up-regulated (FIG. 12). The miR's upregulated by this treatment were analyzed further. Stem loop real time PCR (qRT-PCR) was used to validate the most-upregulated miRNAs in several cell lines (MM.1S, LP1, H929, and JJN3). As shown in FIG. 5D, miR-9-5p expression levels increased at 24 hours in a dose dependent manner compared to the control treatment.

Because human miR-9-5p is encoded by three distinct genomic loci (i.e., primary (pri)-miR-9-1 on chromosome 1 (q22), pri-miR-9-2 on chromosome 5 (q14.3), and pri-miR-9-3 on chromosome 15 (q26.1)), the identity of the locus responsible for miR-9up-regulation in response to AR-42 was investigated. Quantitative RT-PCR showed dose dependent changes in all primary transcripts of miR-9-5p in AR-42-treated MM.1S cells, as compared to controls, supporting the idea that all these chromosomal regions contribute to miR-9-5p up-regulation upon AR-42 in MM cells (FIG. 5E).

The CD44 mRNA Binding Protein IG2FBP3 is the Direct Target of miR-9-5p

To determine if CD44 is a direct target of miR-9-5p, a bioinformatic search (Target Scan [38], Pictar [39], and miRDB) was performed for predicted miR-9-5p binding site(s) in CD44 3'UTR. However, none were identified. Moreover, none of the microRNAs identified in our NanoString assay as being upregulated by AR-42 were predicted to bind to CD44 3'UTR (data not shown). Therefore, miR-9-5p may regulate CD44 expression in an indirect fashion.

To test this hypothesis, MM.1S cells were transiently transfected with miR-9-5p precursor, or scramble control, and CD44 mRNA levels were measured by qRT-PCR after 48 hours. FIG. 7A shows that in the miR-9-5p transfected cells (+) CD44 expression is about 30% lower when compared to scramble control transfected cells (−). In the reciprocal experiment, MM.1S cells were transiently transfected with antago-miR-9 (AS miR-9), or scramble control (AS miR-SCR) and CD44 surface expression was measured.

As shown in FIG. 7B, inhibition of the endogenous miR-9-5p increased more than two times the population with high CD44 expression when compared to cells transfected with scramble sequence (SCR). These results indicate that miR-9-5p regulates CD44 expression in MM cells.

Two related RNA binding proteins, IGF2BP1 and IGF2BP3, were analyzed. These proteins are known to bind and control CD44 mRNA stability [40] in several cellular system and their expression is tightly related to CD44 levels in several forms of cancer [41]. STRING data analysis (http://string-db.org) shows strong functional interaction between IGF2BP1, IGF2BP3, and CD44 (FIG. 7C). Using Targetscan [38], Pictar [39], and RNA22 [42] searches, we identified a highly conserved consensus sequence for miR-9-5p in the 3'UTR of IGF2BP3, and a lower probability site in the 3'UTR of IGF2BP1 (FIG. 7D and data not shown).

To test if IGF2BP1 and IGF2BP3 are bona fide targets of miR-9-5p, MM cells were transfected with miR-9-5p precursor, or scramble control and IGF2BP1 and IGF2BP3 protein expression was measured by Western blot. Ectopic expression of miR-9-5p led to a strong decrease of IGF2BP3 protein paralleled by downregulation of CD44 protein, while the expression of IGF2BP1 was not affected (FIG. 7E). Ectopic expression of another microRNA identified in the NanoString experiment (miR-16) did not influence the protein levels of IGF2BP3, CD44, or IGF2BP1 (FIG. 7E) indicating the specific role of miR-9-5p.

To examine if miR-9-5p targets IGF2BP3 directly, the IGF2BP3 3'UTR containing either the wild type (Wt) or mutated (Mut) miR-9-5p site was cloned into a pGL3-control luciferase vector. Luciferase activity significantly decreased when the Wt reporter construct was co-transfected into MM.1S cells with miR-9-5p, as compared to scramble control (scr) (FIG. 7F). This effect was not observed when IGF2BP3 3'UTR with a specific deletion of 2 nucleotides (Mut) in miR-9-5p consensus sequence was tested (FIG. 7F). These data indicate that CD44 expression can be modulated by changes in miR-9-5p levels, although indirectly. Furthermore, miR-9-5p directly targets IGF2BP3 (but not IGF2BP1), a stabilizer of CD44 mRNA [40].

AR-42 Treatment Sensitizes MM Cells to Lenalidomide

Annexin V staining of MM.1S and MM.1R cells (FIG. 7A and data not shown), the addition of AR-42 (0.1 μM) to Len (2.5 μM) resulted in a 4.9-fold increase in apoptosis at 48 hours, relative to lenalidomide (Len) alone, while the combination of 0.1 μM AR-42 and 5.0 μM Len resulted in a 5.8-fold increase (FIG. 9A). MM.1S cells were treated with 0.1 and 0.2 μM AR-42 in combination with different concentrations of Len (1-10 μM) and their effects were measured in a cell proliferation assay (MTT). To calculate combination indices (CI) we utilized the Chou-Talalay method [43]. We found that the combination of AR-42 with Len showed strong synergism (CI<1) in killing of MM.1S cells (FIG. 13). CD44 up-regulation in MM cells is associated with resistance to lenalidomide [26].

Since MM cell survival is strongly dependent on microenvironment [44-46], the effects of AR-42 in combination with Len on MM cell killing in the context of the bone marrow (BM) milieu was examined. Total BM samples obtained from 5 Len-refractory MM (patients 1, 2, 3, 4, and 7) and 3 newly diagnosed MM patients (patients 5, 6, and 8) were treated with AR-42 (0.2 μM) and Len (5 μM) as single agents, and in combination. Following 48 hours of treatment, multiparametric flow cytometry (diagrammed in FIG. 9B) showed a substantial increase of Annexin V staining, specifically in the CD138+/CD38high MM cells [47, 48] treated with AR-42 in combination with Len (p<—0.0001) (FIG. 9C). In contrast, the CD138neg/CD38low BM cellular fraction did not demonstrate significant evidence of apoptosis following the combination treatment (FIG. 9D). In addition, peripheral blood mononuclear cells (PBMCs) under the same experimental conditions did not show induction of apoptosis (FIG. 6). The BM cells from the same patients were used to assess CD44 expression at 24 hrs after AR-42 treatment. Downregulation of CD44 was observed in the whole BM of all 5 Len-refractory and 2 of the 3 newly diagnosed MM patients (patients 5 and 8) (FIG. 8).

AR-42 Treatment Sensitizes MM Cells to Lenalidomide In Vivo

To investigate the effect of AR-42 and Len in vivo, NOD-SCID mice (n=40) were intravenously injected with $5 \times 10^6$ GFP+/Luc+ MM.1S cells [49]. After three weeks, mice with similar tumor burden were selected and divided into 4 treatment groups (5 mice per group): AR-42 alone, Len alone, AR-42/Len, and vehicle control (VE) (8% DMSO in PBS). To minimize toxicity and investigate a clinically relevant treatment regimen, mice were treated with Len (50 mg/kg) or VE by intraperitoneal injections daily, and AR-42 (25 mg/kg) or VE 3 times per week for 3 weeks. Following treatments, tumors were markedly suppressed in all AR-42/Len treated mice compared to control and single agent [AR-42 vs. Ctrl (p=0.5); Len vs. Ctrl (p=0.014); AR-42/Len vs. Len (p=0.0145); AR-42/Len vs. AR-42 (p=0.0002)] (FIG. 10A-10B). The extent of BM engraftment was determined by flow cytometry using a human anti-CD138 antibody, and it was evident that AR-42/Len treated mice showed significantly less BM engraftment compared to the other treatment groups [AR-42 vs. Ctrl (p=0.8); Len vs. Ctrl (p=0.8); AR-42/Len vs. Len (p=0.016); AR-42/Len vs. AR-42 (p=0.01)] (FIG. 10C).

All mice treated with the AR-42/Len combination displayed a longer survival when compared to the mice treated with either single agent. All treated mice appeared healthy and remained alive past the point at which the last mice in all other treatment groups were removed (FIG. 10D-10E). This data shows that AR-42 in combination with lenalidomide substantially increases lenalidomide sensitivity of MM cells, for example, in the BM environment and other organ systems which would lead to the death of the test animals.

AR-42 Treatment Sensitizes MM Cells to IMiD's In Vitro and In Vivo.

MM.1S and MM.1L-R cells were treated with 0.1 µM or 0.2 µM AR-42 in combination with different concentrations of Len and pomalidomide (1-10 µM) and their effects, were measured by both by Annexin-V/PI and cell proliferation (MTT) assays. The Chou-Talalay method was used to calculate combination indices (CI). The combination of AR-42 with Len and pomalidomide showed strong synergism (CI<0.5) in killing of both MM cell lines. Following 48 hours of treatment, multiparametric flow cytometric analysis showed a significant increase in Annexin-V positive cells in the CD138+/CD38high MM cells (37, 38) (FIGS. 10A-B) treated with AR-42 in combination with Len (p=0.015), while the CD-138neg/CD38low BM cellular fraction and PBMC did not have significant evidence of apoptosis following combination treatment. In vivo data using a previously described homing model show that all mice treated with the AR-42/Len combination remained alive past the point at which the last mice in all other treatment groups were removed [AR-42 vs. Ctrl (p=0.4); Len vs. Ctrl (p=0.08); Len+AR-42 vs. Ctrl (p<0.0001); Len+AR-42 vs. AR-42 (0.0025); Len+AR-42 vs. Len (p=0.03)])(FIGS. 10D-10E).

AR-42 and Pomalidomide

The combination of AR-42 and pomalidomide is well tolerated, does not result increased treatment associated mortality, and increases survival secondary to the anti-cancer effect in a MM mouse model.

To investigate whether the oral combination treatment of AR-42 and pomalidomide improves the survival of mice engrafted with MM cells, 40 NOD-SCID mice were engrafted with $10\times10^6$ MM.1S GFP/Luc+ cells by intravenous injection (IV). Ten days later, mice with the same tumor burden (as calculated by luminescence) (FIG. 14C) were randomly divided into 4 treatment groups (10 mice per group): AR-42 alone, pomalidomide alone, AR-42+pomalidomide, and vehicle control (Ctrl, 8% DMSO in PBS). Mice were treated by oral administration (gavage) daily with pomalidomide (25 mg/kg) or Ctrl, and three times a week (Mon-Tues-Fri) with AR-42 (25 mg/kg) or Ctrl, until elimination criteria, including paralysis, extreme weight loss and dehydration, were reached.

The data demonstrates that the survival of mice treated with AR42+ pomalidomide is significantly improved (log rank test p-value=0.0014) over those treated with AR42 alone (hazard ratio (HR): 0.17, 95% CI: 0.04-0.65), pomalidomide alone (HR=0.14, 95% CI: 0.04-0.52), or neither active treatment (HR: 0.08, 95% CI: 0.02-0.33) (FIG. 14D). By 60 days of observation, all mice have died. Median survival was 52 days (95% CI: 28-55) in the combination group, compared to 42 days for the AR-42 and pomalidomide alone groups and 41 days in the control group. One AR-42+ pomalidomide treated mouse died after 25 days of treatment for non-disease related reasons and was censored.

While toxicity evaluation of IMiD therapy in mice is hindered due to CRBN gene sequence variations in mice vs humans, our in vivo data demonstrate that mice treated with the combination AR-42+ pomalidomide regimen showed improved fitness associated with improved survival.

Effect of HDAC Inhibitors on Apoptosis and Cell Necrosis In Vitro

FIG. 15 shows the effects of three HDAC inhibitors (SAHA, AR-42 and JQ12) in U266, RPMI, and MM1S cells in vitro following treatment with the HDAC inhibitors for 24 and 48 hours at 0.25, 0.5, and 1 µM concentration. Apoptosis was measured by annexin staining while cell necrosis was measured by propidium iodide staining. As shown in FIG. 15, AR-42 achieved the highest level of apoptosis with the lowest levels of cell necrosis while SAHA had a limited impact on apoptosis. No dose response curve could be obtained with panobinostat (LDH, data not shown).

In another aspect, AR-42 can be administered to the patient in an amount of 40 mg three times weekly, 3 weeks on, one week off. In one aspect, lenalidomide can be administered to the patient in an amount of 25 mg per day for days 1-21 of a 28 day cycle. In another aspect, pomalidomide can be administered to the patient in an amount of 4 mg per day for days 1-21 of a 28 day cycle.

AR-42 and an IMiD, as described herein, can be administered to patient in need of treatment (e.g., a patient having MM in need of treatment).

As used herein, the term "substantially" refers to "most of," a "majority of," or at least 50%, 60%, 70%, 80%, and 90% of the amount of, for example, of a mammal that does not have MM.

The terms "treat," "reduce," "suppress," "inhibit," "prevent," or similar terms, as used herein, do not necessarily mean 100% or complete treatment or prevention. Rather, these terms refer to various degrees of treatment or prevention of a particular disease (e.g., 100%, 90%, 80%, 70%, 60%, 50%, 40%, 30%, 20%, 10%, 5%, or 1%) as recognized in the art as being beneficial.

The terms "treatment" or "prevention" also refer to delaying onset of a disease for a period of time or delaying onset indefinitely. The term "treatment" or "treating" refers to administering a drug or treatment to a patient or prescribing a drug to a patient (e.g., by a doctor, nurse, or other medical professional) where the patient or a third party (e.g., caretaker, family member, or health care professional) administers the drug or treatment.

The term "amount effective" refers to an amount of a drug or treatment (e.g., AR-42, IMiD) that will treat, reduce, suppress, inhibit, prevent disease(s) or condition(s) (e.g., MM) or prolong survival of a mammal with a disease or condition.

The term "prolong" or "prolonging" as used herein, refers to increasing time of survival of a mammal receiving treatment compared to a mammal that does not receive treatment. In this aspect, "prolonged survival" can refer to increasing the lifespan of the mammal by, for example, 1%, 5%, 10%, 20%, 30%, 40%, 50%, 60%, 70%, 80% or 90% of the lifespan of mammal that does not have MM.

AR-42 and IMiDs as described herein can be administered orally, parenterally (IV, IM, depot-IM, SQ, and depot-SQ), sublingually, intranasally (inhalation), intrathecally, topically, or rectally. Dosage forms known to those of skill in the art are suitable for delivery of AR-42 and IMiDs as described herein.

In one aspect, AR-42 and an IMiD can be administered in an oral dosage form (e.g., pill, capsule, caplet, or tablet, etc.) to a patient diagnosed with MM.

AR-42 and IMiDs can be formulated into suitable pharmaceutical preparations such as tablets, capsules, or elixirs for oral administration or in sterile solutions or suspensions for parenteral administration. AR-42 and IMiDs as described herein can be formulated into pharmaceutical compositions using techniques and procedures well known in the art.

In one aspect, about 0.1 to 1000 mg, about 5 to about 100 mg, or about 10 to about 50 mg of AR-42 and/or an IMiD, or a physiologically acceptable salt or ester can be compounded with a physiologically acceptable vehicle, carrier, excipient, binder, preservative, stabilizer, flavor, etc., in a unit dosage form as called for by accepted pharmaceutical practice. The amount of active substance in compositions or preparations comprising AR-42 and an IMiD is such that a suitable dosage in the range indicated is obtained.

In another aspect, the compositions can be formulated in a unit dosage form, each dosage containing from about 1 to about 500 mg, or about 10 to about 100 mg of the active ingredient. The term "unit dosage from" refers to physically discrete units suitable as unitary dosages for human subjects and other mammals, each unit containing a predetermined quantity of active material calculated to produce the desired therapeutic effect, in association with a suitable pharmaceutical excipient.

In one aspect, AR-42 and/or an IMiD is mixed with a suitable pharmaceutically acceptable carrier to form compositions. Upon mixing or addition of the compound(s), the resulting mixture may be a solution, suspension, emulsion, or the like. Liposomal suspensions or any other nanoparticle delivery system may also be used as pharmaceutically acceptable carriers. These may be prepared according to methods known to those skilled in the art. The form of the resulting mixture depends upon a number of factors, including the intended mode of administration and the solubility of the compound in the selected carrier or vehicle. In one aspect, the effective concentration is sufficient for lessening or ameliorating at least one symptom of the disease, disorder, or condition treated and may be empirically determined.

Pharmaceutical carriers or vehicles suitable for administration of the AR-42 and/or an IMiD described herein include any such carriers suitable for the particular mode of administration. In addition, the active materials can also be mixed with other active materials that do not impair the desired action, or with materials that supplement the desired action, or have another action. The compounds may be formulated as the sole pharmaceutically active ingredient in the composition or may be combined with other active ingredients.

In another aspect, if AR-42 or an IMiD exhibits insufficient solubility, methods for solubilizing may be used. Such methods are known and include, but are not limited to, using co-solvents such as dimethylsulfoxide (DMSO), using surfactants such as TWEEN, and dissolution in aqueous sodium bicarbonate. Derivatives of the compounds, such as salts or prodrugs, may also be used in formulating effective pharmaceutical compositions.

The concentration of the compound is effective for delivery of an amount upon administration that lessens or ameliorates at least one symptom of the disorder for which the compound is administered. Typically, the compositions are formulated for single dosage administration.

In another aspect, AR-42 and/or an IMiD as described herein may be prepared with carriers that protect them against rapid elimination from the body, such as time-release formulations or coatings. Such carriers include controlled release formulations, such as, but not limited to, microencapsulated delivery systems. The active compound can be included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo model systems for the treated disorder.

In another aspect, AR-42 and/or an IMiD and compositions described herein can be enclosed in multiple or single dose containers. The enclosed compounds and compositions can be provided in kits, for example, including component parts that can be assembled for use. For example, AR-42 and/or an IMiD in lyophilized form and a suitable diluent may be provided as separated components for combination prior to use. A kit may include AR-42 and one or more IMiDs for co-administration. AR-42 and one or more IMiDs may be provided as separate component parts. A kit may include a plurality of containers, each container holding one or more unit dose of the compounds described herein. In one aspect, the containers can be adapted for the desired mode of administration, including, but not limited to tablets, gel capsules, sustained-release capsules, and the like for oral administration; depot products, pre-filled syringes, ampoules, vials, and the like for parenteral administration; and patches, medipads, creams, and the like for topical administration.

The concentration of AR-42 and/or an IMiD in the pharmaceutical composition will depend on absorption, inactivation, and excretion rates of the active compound, the dosage schedule, and amount administered as well as other factors known to those of skill in the art.

In another aspect, the active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound can be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition.

The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

The active materials can also be mixed with other active materials that do not impair the desired action, or with materials that supplement the desired action. AR-42 and/or IMiDs can be used, for example, in combination with an antitumor agent, bisphosphonates, growth factors including erythropoietin and colony stimulating factors, a hormone, a steroid (dexamethasone, prednisone), proteasome inhibitor, or a retinoid. The antitumor agent may be one of numerous chemotherapy agents (e.g., alkylating agent, an antimetabolite, a hormonal agent, melphalan, cyclophosphamide, *vinca* alkaloid, vincristine, procarbazine, hydroxyurea, doxorubicin, liposomal doxorubicin, mitoxantrone, nitrosourea or an imidazole carboxamide).

In one aspect, solutions or suspensions used for parenteral, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerin, propylene glycol, or other synthetic solvent; antimicrobial agents such as benzyl alcohol and methyl parabens; antioxidants such as ascorbic acid and sodium bisulfate; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include, but are not limited to, physiological saline, phosphate buffered saline (PBS), and solutions containing thickening and solubilizing agents such as glucose, polyethylene glycol, polypropyleneglycol, and mixtures thereof. Liposomal suspensions, or any other nanoparticle delivery system, including tissue-targeted liposomes may also be suitable as pharmaceutically acceptable carriers. These may be prepared according to methods known in the art.

In another aspect, AR-42 and/or IMiDs may be prepared with carriers that protect the compound against rapid elimination from the body, such as time-release formulations or coatings. Such carriers include controlled release formulations, such as, but not limited to, implants and microencapsulated delivery systems, and biodegradable and biocompatible polymers such as collagen, ethylene vinyl acetate, polyanhydrides, polyglycolic acid, polyorthoesters, polylactic acid, and the like. Methods for preparation of such formulations are known to those skilled in the art.

In yet another aspect, compounds employed in the methods of the disclosure may be administered enterally or parenterally. When administered orally, compounds employed in the methods of the disclosure can be administered in usual dosage forms for oral administration as is well known to those skilled in the art. These dosage forms include the usual solid unit dosage forms of tablets and capsules as well as liquid dosage forms such as solutions, suspensions, and elixirs. When the solid dosage forms are used, they can be of the sustained release type so that the compounds employed in the methods described herein need to be administered only once or twice daily.

The oral dosage forms can be administered to the patient 1, 2, 3, or 4 times daily. AR-42 and/or the IMiDs described herein can be administered either three or fewer times, or even once or twice daily. Hence, the compounds employed in the methods of the disclosure be administered in oral dosage form. Whatever oral dosage form is used, they can be designed so as to protect the compounds employed in the methods described herein from the acidic environment of the stomach. Enteric coated tablets are well known to those skilled in the art. In addition, capsules filled with small spheres each coated to protect from the acidic stomach, are also well known to those skilled in the art.

It should be apparent to one skilled in the art that the exact dosage and frequency of administration will depend on the particular compounds employed in the methods of the disclosure administered, the particular condition being treated, the severity of the condition being treated, the age, weight, general physical condition of the particular patient, and other medication the individual may be taking as is well known to administering physicians who are skilled in this art.

EXAMPLES

The following non-limiting examples illustrate aspects described herein.

Example 1

Cell Lines

MM cell lines MM.1S Include MM.1R and JJN3 myeloma cell lines, NCI-H929, KMS11, KMS18, OPM2, EJM, LP1, RPMI8226, U266 andL363 (courtesy of Dr. M. Kuehl; National Cancer Institute) were cultured in RPMI-1640 medium supplemented with 10% heat-inactivated fetal bovine serum (FBS). HeLa (CCL-2) and 293T (CRL-3216) were obtained from American Type Cell Collection (ATCC) and maintained in DMEM with 10% FBS.

Example 2

MM Cell Line Transfections

One million of MM.1S, U266, or L363 cells were transfected by electroporation using Nucleofector 4D system (Lonza). Specific nucleofection solutions and programs were optimized for each cell line. Briefly, cells were resuspended in 100 µl of the nucleofector solution SF, 30 pmols of microRNA (miR-9-5p precursor), antagomiR-9, miR-16-5p, negative control miR precursor, or siRNAs (Drosha, or scramble control) were added and transferred to a cuvette. All RNA reagents were from Life Technologies. Program DS-137 was used for MM.1S cells, program DN-100 for U266 and program DS-100 for L363. After electroporation, cells were immediately plated out in pre-warmed medium onto 6 well plates. AR-42 treatments were performed 24 hrs later.

Example 3

CD138+ Plasma Cell Purification

CD138+ plasma cells (PCs) were purified from total bone marrow of patients by Human WholeBlood CD138+ Selection Kit (Cat#18387, Stem Cell Technologies), according to the manufacturer's instructions. Yield and purity of CD138+ cells was evaluated by flow cytometry using anti-CD138 antibody (Becton Dickinson).

Example 4 miRNA and mRNA Profiling

Total RNA was prepared using TRIzol (Invitrogen). The RNA was analyzed by nCounter GX Human Immunology Kit, or nCounter Human microRNA Kit, as recommended by the manufacturer (NanoString Technologies, Inc.). A total of 511 immunology related genes and 800 microRNAs were profiled.

Example 5

Bioinformatic Analyses

Samples analyzed by NanoString assay were normalized using the variance stabilization. The mean linkage hierarchical clustering algorithm was conducted to identify subgroups of significant miRNAs [69]. These results have been obtained using both the Rank Product package (version 2.16.0) of the BioConductor Library, under the R System and the Rank Product library in connection to the cluster analysis module of the Tmev system [70]. The obtained data were deposited in the GEO database (accession number).

Example 6

Enzyme-Linked Immunosorbent Assay (ELISA)

Blood from xenografted mice (0.6 ml/kg) was collected by retro-orbital bleeding and serum was obtained by centrifuging it at 1500×g for 10 min. ELISA was conducted as described by the manufacturer (Abcam). Briefly, serum was diluted 1:40 in Standard Diluent Buffer and 100 µl of each sample was plated in duplicate onto a 96-well plate. Standard and 1× control solution were added to the appropriate wells and incubated for 1 hr. All incubations were conducted at room temperature, unless otherwise noted. The plate was washed, biotinylated anti-CD44 added to each well and plate was incubated for 30 min. The plate was washed again and 100 µl 1× Streptavidin-HRP solution was added into each well, allowed to stand for 30 min. and washed again. Chromogen TMB substrate (100 µl) was added to each well and incubated in the dark for 15 min. Finally, 100 µDwell of Stop Reagent was added and absorbance was read on a spectrophotometer at 450 nm. Soluble CD44 (sCD44) content was calculated based on the readings from the standard and sample dilution factor.

Example 7

Immunoblotting

Cells were harvested by centrifugation, washed with PBS and lysed using buffer composed of 50 mM Tris (pH 7.5), 150 mM NaCl, 10% glycerol, 1.0% NP-40, 0.1% SDS, supplemented with protease and phosphatase inhibitors. Protein concentrations were estimated by Bradford assay and equivalent quantities of the lysates were resolved on 4-20% Tris-HCl SDS-PAGE TGX gels (Bio-Rad). Proteins were transferred to nitrocellulose membranes and stained for acetyl-histone H3 (Milipore), acetyl-histone H4 (Milipore), IGF2BP1 (Cell Signaling Technology), IGF2BP3 (IMP-3, Santa Cruz Biotechnology), CD44 (Santa Cruz Biotechnology), CD48 (Abcam), Drosha (Cell Signaling Technology), or glyceraldehyde 3-phosphate dehydrogenase (GAPDH, Cell Signaling Technology), followed by anti-mouse, or anti-rabbit IgG-HRP (GE Healthcare). Signals were developed using Pierce ECL Western Blotting Substrate (Thermo Fisher Scientific).

Example 8

DNA Constructs

Human CD44 promoter-luciferase reporter gene (CD44P pGL3) [71] was obtained from Addgene (Plasmid 19122). The 3'UTR of CD44 was PCR amplified using following primers:
(Forward) 5'-gctagcCACCTACACCATTATCTTG-3' (SEQ ID NO: 1) and 5'- gctagcAATTCTTGGTGTTGT-TATG-3' (SEQ ID NO: 2) (engineered Nhel sites are in lower case), and the products were cloned into Xbal site downstream from the luciferase gene in pGL3-control vector (Promega). To generate IGF2BP3 luciferase reporter constructs, the 3'UTR was amplified by PCR using primers: (Forward) 5'-TCTTTGGTTATCTAGCTGTATGA-3' (SEQ ID NO: 3) and (Reverse) 5'-TCTTTGGTTATCTAGCTG-TATGA-3' (SEQ ID NO: 3), and cloned into Xbal site of pGL3-control vector (Promega). Mutations in the miR-9-5p binding site of the IGF2BP3 3'UTR were introduced by the QuikChange Mutagenesis Kit (Stratagene) and the following primers:
(Forward) 5'-CAGAGGCAGATGCCAAACGGGG TACAGATTG CTTAACC-3' (SEQ ID NO: 4) and (Reverse) 5'-GGTTAAGCAATCTGTACCCCGTTTG-GCATCTGCCTCTG-3' (SEQ ID NO: 5).

```
(Forward)
5'-CAGAGGCAGATGCCAAACGGGGTACAGATTGCTTAACC-3'
and (Reverse)
5'-GGTTAAGCAATCTGTACCCCGTTTGGCATCTGCCTCTG-3'.
```

Example 9

Luciferase Assay

Hela and 293T cells were transfected with 500 ng of 3'UTR-pGL3-control plasmid and 50 ng of Renilla luciferase expression construct (pRL-TK; Promega), using Lipofectamine 2000 (Invitrogen). After 24 hrs cells were lysed and tested by Dual Luciferase Assay (Promega), according to the manufacturer's instructions. MM.1S cells were transfected with 1.8 μg of pGL3-based luciferase vector and 200 ng of pRL-TK, harvested 24 hrs later and assayed as above.

Example 10 mRNA and miRNA Expression

Quantitative real time-PCR (qRT-PCR) was performed with the TaqMan method (Applied Biosystems), according to the manufacturer's instructions, and analyzed with the 7900HT Sequence Detection System (Applied Biosystems). The appropriate TaqMan probes for mRNA, miRNA, and pri-miRNA quantification were purchased from Applied Biosystems, and all reactions were performed in triplicate. The following probes were used: hsa-miR-9-5p (000583), hsa-mir-9-1 (Hs03303201_pri), hsa-miR-9-2 (Hs03303202_pri), hsa-mir-9-3 (Hs03293595_pri), CD44 (Hs01075861_m1), IGF2BP3 (Hs00559907_g1). Simultaneous quantification of ornithine decarboxylase antizyme 1 (OAZ1), or GAPDH mRNAs were used as a reference for mRNA data normalization, while small endogenous nucleolar RNA U44/U48, or U6 were used for miRNA normalization. The relative expression levels were calculated by the comparative cycle threshold (Ct) method (User Bulletin #2; Applied Biosystems). Expression analyses of pre-miRNA was performed with SYBR green PCR master mix (Applied Biosystems) and normalized for U6 RNA. All primers used for amplification steps are listed in the Supplementary materials and methods.

Example 11

Flow Cytometry

CD44 surface expression was analyzed by staining cells with CD44-FITC antibody (BD Biosciences) for 30 min. in the dark, at room temperature. Apoptosis was measured by Annexin V-FITC and Propidium Iodide (PI) (Clontech) staining for 15 min. in the dark, at room temperature and data immediately acquired on a Beckman Coulter FC500 (Beckman Coulter) machine. Analysis was conducted using the FlowJo Software vX.0.7 (Tree Star Inc.). For the multiparametric analysis, the bone marrow samples were stained with CD38-PE (347687; BD Bioscience), CD138-APC (347193; BD Bioscience), CD45-ECD (A07784; Beckman Coulter), CD44-FITC (BD Bioscience) and AnnexinV-FITC (Clontech) for 30 minutes, washed with PBS and immediately analyzed with Gallios cytometer (Beckman Coulter).

Example 12

Proliferation Assay

Cell proliferation was assessed using the MTT cell proliferation assay (Promega) according to the manufacturer's protocol.

Example 13

Animal Experiments

Animal experiments were performed according to OSU institutional guidelines. To generate MM xenograft model, 1×10$^7$ viable MM.1S cells were injected subcutaneously into the right flank of 12 5-week-old female nude mice (Foxn1nu/Foxn1nu; Charles River). The tumor size was measured once a week using a caliper, and the volume was calculated in cubed millimeters (mm3), using the formula L×W2/2. At 3 weeks after injection, a group of 8 mice with comparable tumor size (250±60 mm3) were randomly divided into two groups, using 4 mice for each treatment. Mice were treated with intra-tumoral injection of AR-42 (25 mg/kg) or DMSO (8% in PBS) once a day on Monday and Wednesday. The day after the second treatment, when the tumor sizes between the 2 different groups were comparable, blood from mice was collected by retro-orbital bleeding and the mice were sacrificed for IHC analysis.

For studies involving AR-42 combination with lenalidomide, GFP+/Luc+MM.1S stable line [49] was harvested during logarithmic growth phase, washed with PBS and injected intravenously into NOD-SCID nude mice (5×10$^6$ cells in 0.2 ml/mouse) under general anesthesia (isoflurane, 2-4% to effect). Beginning at 7 days post-injection, mice were monitored every day for the appearance of tumors by fluorescence using in vivo Imaging System (IVIS). On day 15, when the engraftment reached approximately ≥2×10$^6$ photons/sec/cm2/sr mice with similar tumor burden were divided into different groups of treatments. Intraperitoneal injections with vehicle control (8% DMSO in PBS), AR-42 (25 mg/kg; Mon-Tue-Fri) and lenalidomide (50 mg/kg, daily) were administered by intraperitoneal injection under general anesthesia (isoflurane, 2-4% to effect). Treatments for each mouse continued for 3 weeks, which ended when the control group showed sign of disease, including paralysis and extreme weight lost, or when tumor mass was equivalent to 10% of body weight.

Example 14

Detection of Tumor Progression by Bioluminescence Imaging

Mice were injected with 75 mg/kg Luciferin (Xenogen), and tumor growth was detected by bioluminescence 10 min. after the injection. The home-built bioluminescence system used an electron multiplying charge-coupled device (Andor Technology Limited) with an exposure time of 30 sec. and an electron multiplication gain of 500 voltage gain×200, 5-by-5 binning, and with background subtraction. Images were analyzed using ImageJ software (National Institutes of Health).

Example 15

Immunohistochemistry

Xenograft tumor samples were fixed in 10% neutral-buffered formalin embedded in paraffin, and sectioned at 4 μm. Slides were then placed in a 60° C. oven for 1 hr, cooled, deparaffinized, and rehydrated by passing slides through xylene, a series of graded ethanol solutions, and ending with water. All slides were placed for 5 min in a 3% hydrogen peroxide solution to block the endogenous peroxidase. Antigen retrieval was performed by heat induced epitope retrieval (HIER), in a citric acid solution, pH 6.1, for 25 min at 96° C. followed by cooling down for 15 min. Slides were placed on a Dako Autostainer and sections were treated with primary antibodies for human CD138 and CD44 followed by biotinylated secondary antibodies and the DAB chromogen.

Example 16

Statistics

All preclinical data were obtained from at least three independent experiments and are expressed as mean±standard deviation (SD). Comparisons between groups were performed using two-tailed t-tests, and comparisons between multiple groups were performed using 1-way analysis of variance (ANOVA).

Mouse data were evaluated by ANOVA, and synergy between AR-42 and Len was tested by interaction contrast. To investigate Annexin-V and CD44 level in primary patient samples, geometric mean values were analyzed by using mixed effect model and incorporated repeated measures for each sample. For the Annexin-V experiment, p-values were adjusted by Holm's method to control the familywise error rate at 0.05. Other P values reported in the manuscript were obtained by 2 tail t-test.

Example 17

Dosing Regimens

Exemplary dosing regimens are provided. The single agent dose of AR-42 in patients with multiple myeloma is 40 mg taken three times weekly for three weeks followed by one week off. The recommended phase 2 dose of AR-42 was 40 mg TIW (three times per week) (120 mg/wk), and the dose intensity of AR-42 in the combination of AR-42 and pomalidomide to be explored ranges from 80-150 mg/wk using both twice and three times weekly administration. Pomalidomide dose levels will be 2-4 mg daily for 21 days of a 28 day treatment cycle.

REFERENCES

1. Fonseca R, San Miguel J. Prognostic factors and staging in multiple myeloma. Hematology/oncology clinics of North America. 2007; 21:1115-1140.
2. Fonseca R, Bergsagel P L, Drach J, Shaughnessy J, Gutierrez N, Stewart A K, Morgan G, Van Ness B, Chesi M, Minvielle S, Neri A, Barlogie B, Kuehl W M, Liebisch P, Davies F, Chen-Kiang S, et al. International Myeloma Working Group molecular classification of multiple myeloma: spotlight review. Leukemia. 2009; 23:2210-2221.
3. Kapoor P, Kumar S, Fonseca R, Lacy M Q, Witzig T E, Hayman S R, Dispenzieri A, Buadi F, Bergsagel P L, Gertz M A, Dalton R J, Mikhael J R, Dingli D, Reeder C B, Lust J A, Russell S J, et al. Impact of risk stratification on outcome among patients with multiple myeloma receiving initial therapy with lenalidomide and dexamethasone. Blood. 2009; 114:518-521.
4. Nair B, van Rhee F, Shaughnessy J D, Anaissie E, Szymonifka J, Hoering A, Alsayed Y, Waheed S, Crowley J, Barlogie B. Superior results of Total Therapy 3 (2003-33) in gene expression profiling-defined low-risk multiple myeloma confirmed in subsequent trial 2006-66 with VRD maintenance. Blood. 2010; 115:4168-4173.
5. Cavo M, Tacchetti P, Patriarca F, Petrucci M T, Pantani L, Galli M, Di Raimondo F, Crippa C, Zamagni E, Palumbo A, Offidani M, Corradini P, Narni F, Spadano A, Pescosta N, Deliliers G L, et al. Bortezomib with thalidomide plus dexamethasone compared with thalidomide plus dexamethasone as induction therapy before, and consolidation therapy after, double autologous stem-cell transplantation in newly diagnosed multiple myeloma: a randomised phase 3 study. Lancet. 2010; 376:2075-2085.
6. Kumar S K, Rajkumar S V, Dispenzieri A, Lacy M Q, Hayman S R, Buadi F K, Zeldenrust S R, Dingli D, Russell S J, Lust J A, Greipp P R, Kyle R A, Gertz M A. Improved survival in multiple myeloma and the impact of novel therapies. Blood. 2008; 111:2516-2520.
7. Palumbo A, Gay F. Towards a new standard of care for patients with myeloma? The lancet oncology. 2010; 11:3-4.
8. Palumbo A, Falco P, Falcone A, Benevolo G, Canepa L, Gay F, Larocca A, Magarotto V, Gozzetti A, Luraschi A, Morabito F, Nozza A, Knight R D, Zeldis J B, Boccadoro M, Petrucci M T. Melphalan, prednisone, and lenalidomide for newly diagnosed myeloma: kinetics of neutropenia and thrombocytopenia and time-to-event results. Clinical lymphoma & myeloma. 2009; 9:145-150.
9. Gay F, Hayman S R, Lacy M Q, Buadi F, Gertz M A, Kumar S, Dispenzieri A, Mikhael J R, Bergsagel P L, Dingli D, Reeder C B, Lust J A, Russell S J, Roy V, Zeldenrust S R, Witzig T E, et al. Lenalidomide plus dexamethasone versus thalidomide plus dexamethasone in newly diagnosed multiple myeloma: a comparative analysis of 411 patients. Blood. 2010; 115:1343-1350.
10. Lionetti M, Agnelli L, Mosca L, Fabris S, Andronache A, Todoerti K, Ronchetti D, Deliliers G L, Neri A. Integrative high-resolution microarray analysis of human myeloma cell lines reveals deregulated miRNA expression associated with allelic imbalances and gene expression profiles. Genes Chromosomes Cancer. 2009; 48:521-531.
11. Lionetti M, Biasiolo M, Agnelli L, Todoerti K, Mosca L, Fabris S, Sales G, Deliliers G L, Bicciato S, Lombardi L, Bortoluzzi S, Neri A. Identification of microRNA expression patterns and definition of a microRNA/mRNA regulatory network in distinct molecular groups of multiple myeloma. Blood. 2009; 114:e20-26.
12. Pichiorri F, Suh S S, Ladetto M, Kuehl M, Palumbo T, Drandi D, Taccioli C, Zanesi N, Alder H, Hagan J P, Munker R, Volinia S, Boccadoro M, Garzon R, Palumbo A, Aqeilan R I, et al. MicroRNAs regulate critical genes associated with multiple myeloma pathogenesis. Proceedings of the National Academy of Sciences of the United States of America. 2008; 105:12885-12890.
13. Maes K, Menu E, Van Valckenborgh E, Van Riet I, Vanderkerken K, De Bruyne E. Epigenetic modulating agents as a new therapeutic approach in multiple myeloma. Cancers. 2013; 5:430-461.
14. Dimopoulos K, Gimsing P, Gronbaek K. The role of epigenetics in the biology of multiple myeloma. Blood cancer journal. 2014; 4:e207.
15. Mitsiades C S, Mitsiades N S, McMullan C J, Poulaki V, Shringarpure R, Hideshima T, Akiyama M, Chauhan D, Munshi N, Gu X, Bailey C, Joseph M, Libermann T A, Richon V M, Marks P A, Anderson K C, et al. Transcriptional signature of histone deacetylase inhibition in multiple myeloma: biological and clinical implications. Proceedings of the National Academy of Sciences of the United States of America. 2004; 101:540-545.
16. Richardson P, Mitsiades C, Colson K, Reilly E, McBride L, Chiao J, Sun L, Ricker J, Rizvi S, Oerth C, Atkins B, Fearen I, Anderson K, Siegel D. Phase I trial of oral vorinostat (suberoylanilide hydroxamic acid, SAHA) in patients with advanced multiple myeloma. Leukemia & lymphoma. 2008; 49:502-507.
17. Damiano J S, Cress A E, Hazlehurst L A, Shtil A A, Dalton W S. Cell adhesion mediated drug resistance (CAM-DR): role of integrins and resistance to apoptosis in human myeloma cell lines. Blood. 1999; 93:1658-1667.

18. Bourguignon L Y, Spevak C C, Wong G, Xia W, Gilad E. Hyaluronan-C D44 interaction with protein kinase C (epsilon) promotes oncogenic signaling by the stem cell marker Nanog and the Production of microRNA-21, leading to down-regulation of the tumor suppressor protein PDCD4, anti-apoptosis, and chemotherapy resistance in breast tumor cells. J Biol Chem. 2009; 284:26533-26546.

19. Chikamatsu K, Ishii H, Murata T, Sakakura K, Shino M, Toyoda M, Takahashi K, Masuyama K. Alteration of cancer stem cell-like phenotype by histone deacetylase inhibitors in squamous cell carcinoma of the head and neck. Cancer science. 2013; 104:1468-1475.

20. Dimopoulos M, Siegel D S, Lonial S, Qi J, Hajek R, Facon T, Rosinol L, Williams C, Blacklock H, Goldschmidt H, Hungria V, Spencer A, Palumbo A, Graef T, Eid J E, Houp J, et al. Vorinostat or placebo in combination with bortezomib in patients with multiple myeloma (VANTAGE 088): a multicentre, randomised, double-blind study. The lancet oncology. 2013; 14:1129-1140.

21. San-Miguel J F, Richardson P G, Gunther A, Sezer O, Siegel D, Blade J, LeBlanc R, Sutherland H, Sopala M, Mishra K K, Mu S, Bourquelot P M, Victoria Mateos M, Anderson K C. Phase Ib study of panobinostat and bortezomib in relapsed or relapsed and refractory multiple myeloma. Journal of clinical oncology: official journal of the American Society of Clinical Oncology. 2013; 31:3696-3703.

22. Biran N, Shahnaz S, Jagannath S, Cho H J, Osman K, Parekh S, Choi D, Garcia K, Catamero D, La L, Gullie J, Chan E, Chari A. A Phase II, Single-Center, Open-Label Study Of Oral Panobinostat In Combination With Lenalidomide and Weekly Dexamethasone In Patients With Multiple Myeloma. Blood. 2013; 122:5392.

23. Richter J R, Bilotti E, McBride L, Schmidt L, Gao Z, Tufail M, Anand P, McNeill A, Bednarz U, Graef T, Vesole D H, Siegel D S. Salvage Therapy with Vorinostat, Lenalidomide, and Dexamethasone (ZRD) in Lenalidomide/Dexamethasone Relapsed/Refractory Multiple Myeloma. ASH Annual Meeting Abstracts. 2011; 118:3986.

24. Kulp S K, Chen C S, Wang D S, Chen C Y, Chen C S. Antitumor effects of a novel phenylbutyrate-based histone deacetylase inhibitor, (S)-HDAC-42, in prostate cancer. Clinical cancer research: an official journal of the American Association for Cancer Research. 2006; 12:5199-5206.

25. Zhang S, Suvannasankha A, Crean C D, White V L, Chen C S, Farag S S. The novel histone deacetylase inhibitor, AR-42, inhibits gp130/Stat3 pathway and induces apoptosis and cell cycle arrest in multiple myeloma cells. International journal of cancer Journal international du cancer. 2011; 129:204-213.

26. Bjorklund C C, Baladandayuthapani V, Lin H Y, Jones R J, Kuiatse I, Wang H, Yang J, Shah J J, Thomas S K, Wang M, Weber D M, Orlowski R Z. Evidence of a role for CD44 and cell adhesion in mediating resistance to lenalidomide in multiple myeloma: therapeutic implications. Leukemia. 2014; 28:373-383.

27. Naor D, Sionov R V, Ish-Shalom D. CD44: structure, function, and association with the malignant process. Adv Cancer Res. 1997; 71:241-319.

28. Josefsson A, Adamo H, Hammarsten P, Granfors T, Stattin P, Egevad L, Laurent A E, Wikström P, Bergh A. Prostate cancer increases hyaluronan in surrounding nonmalignant stroma, and this response is associated with tumor growth and an unfavorable outcome. Am J Pathol. 2011; 179:1961-1968.

29. Gritsenko P G, Ilina O, Friedl P. Interstitial guidance of cancer invasion. J Pathol. 2012; 226:185-199.

30. Lee J L, Wang M J, Chen J Y. Acetylation and activation of STAT3 mediated by nuclear translocation of CD44. The Journal of cell biology. 2009; 185:949-957.

31. Vikesaa J, Hansen T V, Jonson L, Borup R, Wewer U M, Christiansen J, Nielsen F C. RNA-binding IMPs promote cell adhesion and invadopodia formation. EMBO J. 2006; 25:1456-1468.

32. Lin T Y, Fenger J, Murahari S, Bear M D, Kulp S K, Wang D, Chen C S, Kisseberth W C, London C A. AR-42, a novel HDAC inhibitor, exhibits biologic activity against malignant mast cell lines via down-regulation of constitutively activated Kit. Blood. 2010; 115:4217-4225.

33. Lucas D M, Alinari L, West D A, Davis M E, Edwards R B, Johnson A J, Blum K A, Hofmeister C C, Freitas M A, Parthun M R, Wang D, Lehman A, Zhang X, Jarjoura D, Kulp S K, Croce C M, et al. The novel deacetylase inhibitor AR-42 demonstrates pre-clinical activity in B-cell malignanciesin vitro and in vivo. PLoS One. 2010; 5:e10941.

34. Woan K V, Sahakian E, Sotomayor E M, Seto E, Villagra A.
Modulation of antigen-presenting cells by HDAC inhibitors: implications in autoimmunity and cancer. Immunology and cell biology. 2012; 90:55-65.

35. Ohwada C, Nakaseko C, Koizumi M, Takeuchi M, Ozawa S, Naito M, Tanaka H, Oda K, Cho R, Nishimura M, Saito Y. CD44 and hyaluronan engagement promotes dexamethasone resistance in human myeloma cells. European journal of haematology. 2008; 80:245-250.

36. Lee Y, Ahn C, Han J, Choi H, Kim J, Yim J, Lee J, Provost P, Rådmark O, Kim S, Kim V N. The nuclear RNase III Drosha initiates microRNA processing. Nature. 2003; 425:415-419.

37. Fortina P, Surrey S. Digital mRNA profiling. Nat Biotechnol. 2008; 26:293-294.

38. Lewis B P, Shih I H, Jones-Rhoades M W, Bartel D P, Burge C B. Prediction of mammalian microRNA targets. Cell. 2003; 115:787-798.

39. Krek A, Gran D, Poy M N, Wolf R, Rosenberg L, Epstein E J, MacMenamin P, da Piedade I, Gunsalus K C, Stoffel M, Rajewsky N. Combinatorial microRNA target predictions. Nat Genet. 2005; 37:495-500.

40. Vikesaa J, Hansen T V, Jonson L, Borup R, Wewer U M, Christiansen J, Nielsen F C. RNA-binding IMPs promote cell adhesion and invadopodia formation. The EMBO journal. 2006; 25:1456-1468.

41. Schaeffer D F, Owen D R, Lim H J, Buczkowski A K, Chung S W, Scudamore C H, Huntsman D G, Ng S S, Owen D A. Insulin-like growth factor 2 mRNA binding protein 3 (IGF2BP3) overexpression in pancreatic ductal adenocarcinoma correlates with poor survival. BMC cancer. 2010; 10:59.

42. Miranda K C, Huynh T, Tay Y, Ang Y S, Tam W L, Thomson A M, Lim B, Rigoutsos I. A pattern-based method for the identification of MicroRNA binding sites and their corresponding heteroduplexes. Cell. 2006; 126:1203-1217.

43. Chou T C. Drug combination studies and their synergy quantification using the Chou-Talalay method. Cancer Res. 2010; 70:440-446.

44. Manier S, Sacco A, Leleu X, Ghobrial I M, Roccaro A M. Bone marrow microenvironment in multiple myeloma progression. Journal of biomedicine & biotechnology. 2012; 2012:157496.

45. Romano A, Conticello C, Cavalli M, Vetro C, La Fauci A, Parrinello N L, Di Raimondo F. Immunological dysregulation in multiple myeloma microenvironment. Biomed Res Int. 2014; 2014:198539.

46. Dalton W S. The tumor microenvironment: focus on myeloma. Cancer Treat Rev. 2003; 1:11-19.

47. Kim D, Park C Y, Medeiros B C, Weissman I L. CD19-CD45 low/–CD38 high/CD138+ plasma cells enrich for human tumorigenic myeloma cells. Leukemia. 2012; 26:2530-2537.

48. Kumar S, Kimlinger T, Morice W. Immunophenotyping in multiple myeloma and related plasma cell disorders. Best practice & research Clinical haematology. 2010; 23:433-451.

49. Roccaro A M, Sacco A, Thompson B, Leleu X, Azab A K, Azab F, Runnels J, Jia X, Ngo H T, Melhem M R, Lin C P, Ribatti D, Rollins B J, Witzig T E, Anderson K C, Ghobrial I M. MicroRNAs 15a and 16 regulate tumor proliferation in multiple myeloma. Blood. 2009; 113:6669-6680.

50. Kraj M, Kopeć-Szlęzak J, Pogłód R, Kruk B. Flow cytometric immunophenotypic characteristics of 36 cases of plasma cell leukemia. Leuk Res. 2011; 35:169-176.

51. Kim I, Uchiyama H, Chauhan D, Anderson K C. Cell surface expression and functional significance of adhesion molecules on human myeloma-derived cell lines. Br J Haematol. 1994; 87:483-493.

52. Ghosh S C, Neslihan Alpay S, Klostergaard J. CD44: a validated target for improved delivery of cancer therapeutics. Expert Opin Ther Targets. 2012; 16:635-650.

53. Skubitz A P. Adhesion molecules. Cancer Treat Res. 2002; 107:305-329.

54. Hao J, Chen H, Madigan M C, Cozzi P J, Beretov J, Xiao W, Delprado W J, Russell P J, Li Y. Co-expression of CD147 (EMMPRIN), CD44v3-10, MDR1 and monocarboxylate transporters is associated with prostate cancer drug resistance and progression. Br J Cancer. 2010; 103:1008-1018.

55. Chen H, Hao J, Wang L, Li Y. Coexpression of invasive markers (uPA, CD44) and multiple drug-resistance proteins (MDR1, MRP2) is correlated with epithelial ovarian cancer progression. Br J Cancer. 2009; 101:432-440.

56. Miletti-Gonzalez K E, Chen S, Muthukumaran N, Saglimbeni G N, Wu X, Yang J, Apolito K, Shih W J, Hait W N, Rodriguez-Rodriguez L. The CD44 receptor interacts with P-glycoprotein to promote cell migration and invasion in cancer. Cancer Res. 2005; 65:6660-6667.

57. Zhao J J, Lin J, Zhu D, Wang X, Brooks D, Chen M, Chu Z B, Takada K, Ciccarelli B, Admin S, Tao J, Tai Y T, Treon S, Pinkus G, Kuo W P, Hideshima T, et al. miR-30-5p functions as a tumor suppressor and novel therapeutic tool by targeting the oncogenic Wnt/β-catenin/BCL9 pathway. Cancer Res. 2014; 74:1801-1813.

58. Al-Hajj M, Wicha M S, Benito-Hernandez A, Morrison S J, Clarke M F. Prospective identification of tumorigenic breast cancer cells. Proc Natl Acad Sci USA. 2003; 100:3983-3988.

59. Bourguignon L Y, Shiina M, Li J J. Hyaluronan-C D44 interaction promotes oncogenic signaling, microRNA functions, chemoresistance, and radiation resistance in cancer stem cells leading to tumor progression. Adv Cancer Res. 2014; 123:255-275.

60. Bourguignon L Y, Earle C, Wong G, Spevak C C, Krueger K. Stem cell marker (Nanog) and Stat-3 signaling promote MicroRNA-21 expression and chemoresistance in hyaluronan/CD44-activated head and neck squamous cell carcinoma cells. Oncogene. 2012; 31:149-160.

61. Hofmeister C C, Liu Z, Bowers M A, Porcu P, Flynn J M, Christian, Baiocchi R A, Benson D M Jr, Andritsos L A, Greenfield C N, Sell M, Geyer S, Byrd J C, Greyer M R. Phase I Study of AR-42 in Relapsed Multiple Myeloma and Lymphoma. ASH Annual Meeting Abstracts, Abstract #2955. 2012.

62. Hideshima T, Cottini F, Ohguchi H, Jakubikova J, Gorgun G, Mimura N, Tai Y T, Munshi N C, Richardson P G, Anderson K C. Rational combination treatment with histone deacetylase inhibitors and immunomodulatory drugs in multiple myeloma. Blood cancer journal. 2015; 5:e312.

63. Zhao C, Sun G, Li S, Shi Y. A feedback regulatory loop involving microRNA-9 and nuclear receptor TLX in neural stem cell fate determination. Nature structural & molecular biology. 2009; 16:365-371.

64. Senyuk V, Zhang Y, Liu Y, Ming M, Premanand K, Zhou L, Chen P, Chen J, Rowley J D, Nucifora G, Qian Z. Critical role of miR-9 in myelopoiesis and EVI1-induced leukemogenesis. Proceedings of the National Academy of Sciences of the United States of America. 2013; 110:5594-5599.

65. Thiele S, Wittmann J, Jack H M, Pahl A. miR-9 enhances IL-2 production in activated human CD4(+) T cells by repressing Blimp-1. European journal of immunology. 2012; 42:2100-2108.

66. Nie K, Gomez M, Landgraf P, Garcia J F, Liu Y, Tan L H, Chadburn A, Tuschl T, Knowles D M, Tam W. MicroRNA-mediated down-regulation of PRDM1/Blimp-1 in Hodgkin/Reed-Sternberg cells: a potential pathogenetic lesion in Hodgkin lymphomas. Am J Pathol. 2008; 173:242-252.

67. Stessman H A, Mansoor A, Zhan F, Linden M A, Van Ness B, Baughn L B. Bortezomib resistance can be reversed by induced expression of plasma cell maturation markers in a mouse in vitro model of multiple myeloma. PLoS One. 2013; 8:e77608.

68. Zoller M. CD44, Hyaluronan, the Hematopoietic Stem Cell, and Leukemia-Initiating Cells. Front Immunol. 2015; 6:235.

69. Huber W, von Heydebreck A, Sultmann H, Poustka A, Vingron M. Variance stabilization applied to microarray data calibration and to the quantification of differential expression. Bioinformatics. 2002; 1:S96-104.

70. Yeung K Y, Medvedovic M, Bumgarner R E. Clustering gene-expression data with repeated measurements. Genome biology. 2003; 4:R34.

71. Godar S, Ince T A, Bell G W, Feldser D, Donaher J L, Bergh J, Liu A, Miu K, Watnick R S, Reinhardt F, McAllister S S, Jacks T, Weinberg R A. Growth-inhibitory and tumor-suppressive functions of p53 depend on its repression of CD44 expression. Cell. 2008; 134:62-73.

73. Chou T C: Drug combination studies and their synergy quantification using the Chou-Talalay method. Cancer Res 70:440-6, 2010

74. Canella A, Cordero Nieves H, Sborov D W, et al: HDAC inhibitor AR-42 decreases CD44 expression and sensitizes myeloma cells to lenalidomide. Oncotarget 6:31134-50, 2015

75. Roccaro A M, Sacco A, Thompson B, et al: MicroRNAs 15a and 16 regulate tumor proliferation in multiple myeloma. Blood 113:6669-80, 2009.

76. Kronke J, Fink E C, Hollenbach P W, et al: Lenalidomide induces ubiquitination and degradation of CKIalpha in del(5q) MDS. Nature 523:183-8, 2015.

77. Tseng Y C, Kulp S K, Lai I L, et al: Preclinical Investigation of the Novel Histone Deacetylase Inhibitor AR-42 in the Treatment of Cancer-Induced Cachexia. J Natl Cancer Inst 107, 2015.

78. Chen et al., Clinical Pharmacokinetics and Pharmacodynamics of Lenalidomide, Clin. Pharmacokinet, Jun. 28, 2016.

Although the above description refers to particular aspects, it is to be understood that these aspects are merely illustrative. It will be apparent to those skilled in the art that various modifications and variations can be made to the methods described herein. Thus, it is intended that the present description include modifications and variations that are within the scope of the appended claims and their equivalents.

What is claimed is:

1. A method of sensitizing multiple myeloma cells to treatment with lenalidomide comprising administering AR-42 and lenalidomide to a patient in need treatment in an amount sufficient to achieve a blood or tissue concentration of at least about 0.5 to about 1 μM of AR-42 and at least about 391 to about 568 ng/ml of lenalidomide.

2. The method of claim 1, wherein the amount of AR-42 administered to the patient is about 40 to 70 mg in a single dose or divided dose, three times per week for three weeks out of a 28 day cycle.

3. The method of claim 2, wherein the amount of AR-42 administered to the patient is about 0.6 to about 1.1 mg/kg of the patient.

4. The method claim 2, wherein the amount of lenalidomide administered to the patient is about 25 mg per day for days 1-21 of a 28 day cycle.

5. A method of treating a mammal with multiple myeloma comprising administering AR-42 and an immunomodulatory agent selected from the group consisting of lenalidomide and pomolidomide to the mammal.

6. The method of claim 5, wherein the amount of AR-42 administered to the mammal is about 40 to 70 mg in a single dose or divided dose, three times per week for three weeks out of a 28 day cycle.

7. The method of claim 6, wherein the amount of AR-42 administered to the patient is about 0.6 to about 1.1 mg/kg of the patient.

8. The method of claim 5, wherein AR-42 and the immunomodulatory agent are co-administered to the mammal.

9. The method of claim 5, wherein AR-42 is administered before administering the immunomodulatory agent.

10. The method of claim 5, wherein the immunomodulatory agent is administered before administering AR-42.

11. The method of claim 5, where the amount of lenalidomide administered to the mammal is about 25 mg per day for days 1-21 of a 28 day cycle.

12. The method of claim 5, where the amount of pomalidomide administered to the mammal is about 4 mg per day for days 1-21 of a 28 day cycle.

* * * * *

UNITED STATES PATENT AND TRADEMARK OFFICE
CERTIFICATE OF CORRECTION

PATENT NO. : 10,022,342 B2  
APPLICATION NO. : 15/254900  
DATED : July 17, 2018  
INVENTOR(S) : Flavia Pichiorri and Craig Hofmeister Page 1 of 1

It is certified that error appears in the above-identified patent and that said Letters Patent is hereby corrected as shown below:

In the Specification

Column 1, Lines 15-18 replace the Government Support Clause with:
--This invention was made with government support under R21 CA156222 awarded by National Institutes of Health. The government has certain rights in the invention.--

Signed and Sealed this  
Eighteenth Day of August, 2020

Andrei Iancu  
*Director of the United States Patent and Trademark Office*